(12) United States Patent
Janata et al.

(10) Patent No.: US 10,822,366 B2
(45) Date of Patent: Nov. 3, 2020

(54) LINCOSAMIDE DERIVATIVES, PREPARATION AND USE THEREOF AS ANTIMICROBIAL AGENT

(71) Applicant: MIKROBIOLOGICKY USTAV AV CR, V. V. I., Prague-Krc (CZ)

(72) Inventors: Jiri Janata, Psary-Dolni Jircany (CZ); Zdenek Kamenik, Prague (CZ); Stanislav Kadlcik, Ratiskovice (CZ); Lucie Najmanova, Prague (CZ); Radek Gazak, Prague-Vychod (CZ)

(73) Assignee: MIKROBIOLOGYICKY USTAV AG CR, V. V. I., KRC (CZ)

( * ) Notice: Subject to any disclaimer, the term of this patent is extended or adjusted under 35 U.S.C. 154(b) by 0 days.

(21) Appl. No.: 16/491,133

(22) PCT Filed: Mar. 9, 2018

(86) PCT No.: PCT/CZ2018/050008
§ 371 (c)(1),
(2) Date: Sep. 4, 2019

(87) PCT Pub. No.: WO2018/161979
PCT Pub. Date: Sep. 13, 2018

(65) Prior Publication Data
US 2020/0017537 A1    Jan. 16, 2020

(30) Foreign Application Priority Data
Mar. 10, 2017 (CZ) .................................. 2017-137

(51) Int. Cl.
C07H 15/18 (2006.01)
(52) U.S. Cl.
CPC .................... *C07H 15/18* (2013.01)

(58) Field of Classification Search
CPC ............................. C07H 15/16; C07H 15/18
See application file for complete search history.

(56) References Cited

U.S. PATENT DOCUMENTS 3,364,197 A    1/1968    Hoeksema

FOREIGN PATENT DOCUMENTS

| CN | 105566411 A | 5/2016 |
| EP | 2166015 A1 | 3/2010 |
| WO | 2010127645 A2 | 11/2010 |

OTHER PUBLICATIONS

Collin et al., Helvetica Chimica Acta, vol. 92 (2009), pp. 230-266.*
International Search Report and Written Opinion of corresponding PCT application No. PCT/CZ2018/050008, dated May 18, 2018.

* cited by examiner

*Primary Examiner* — Alicia L Otton
(74) *Attorney, Agent, or Firm* — Notaro, Michalos & Zaccaria P.C.

(57) ABSTRACT

Lincosamides of general formula I, where R1 is selected from C2-C8 alkyl or C2-C8 alkenyl; R3 is selected from OH, O(C1-C4 alkyl), SH, S(C1-C4 alkyl) or halogen; R4 is H or C1-C3 alkyl; each of R21, R22, R23, R24, R25 is independently selected from the group consisting of H, OH, C1-C4 alkyl, C1-C4 alkenyl, C1-C4 alkynyl, halogen, O(C1-C4 alkyl), O(C1-C4 alkenyl), O(C1-C4 alkynyl), $NH_2$, N(C1-C4 alkyl)$_2$, N(C1-C4 alkenyl)$_2$, N(C1-C4 alkynyl)$_2$; and pharmaceutically acceptable salts thereof. A method of preparation thereof, in particular a biosynthetic method using newly discovered functions of celesticetin biosynthetic proteins Ccb1 and/or Ccb2. Lincosamides of general formula I are suitable for use as antibacterial and antiprotozoal substances.

21 Claims, No Drawings

Specification includes a Sequence Listing.

SEQUENCE LISTING
<160> NUMBER OF SEQ ID NOS: 10
<210> SEQ ID NO 1
<211> LENGTH: 25
<212> TYPE: DNA
<213> ORGANISM: artificial
<220> FEATURE:
<223> OTHER INFORMATION: primer
<400> SEQUENCE: 1
ccgcatatgt ccgacttagc tgccg                25
<210> SEQ ID NO 2
<211> LENGTH: 25

-continued

```
<212> TYPE: DNA
<213> ORGANISM: artificial
<220> FEATURE:
<223> OTHER INFORMATION: primer

<400> SEQUENCE: 2
ccgctcgagg cggggctgcc aggcg                                           25

<210> SEQ ID NO 3
<211> LENGTH: 26
<212> TYPE: DNA
<213> ORGANISM: artificial
<220> FEATURE:
<223> OTHER INFORMATION: primer

<400> SEQUENCE: 3
ctgcatatgc atcttgatcc aaccac                                          26

<210> SEQ ID NO 4
<211> LENGTH: 26
<212> TYPE: DNA
<213> ORGANISM: artificial
<220> FEATURE:
<223> OTHER INFORMATION: primer

<400> SEQUENCE: 4
atagaattct catcggtggt cgtcgc                                          26

<210> SEQ ID NO 5
<211> LENGTH: 27
<212> TYPE: DNA
<213> ORGANISM: artificial
<220> FEATURE:
<223> OTHER INFORMATION: primer

<400> SEQUENCE: 5
aaccccatat gaagcgacgt ggcatgg                                         27

<210> SEQ ID NO 6
<211> LENGTH: 32
<212> TYPE: DNA
<213> ORGANISM: artificial
<220> FEATURE:
<223> OTHER INFORMATION: primer

<400> SEQUENCE: 6
aacccctcga gtaaggtcat gaactccgca cg                                   32

<210> SEQ ID NO 7
<211> LENGTH: 26
<212> TYPE: DNA
<213> ORGANISM: artificial
<220> FEATURE:
<223> OTHER INFORMATION: primer

<400> SEQUENCE: 7
ctacatatga agacgcccgg tacatc                                          26

<210> SEQ ID NO 8
<211> LENGTH: 26
<212> TYPE: DNA
<213> ORGANISM: artificial
<220> FEATURE:
<223> OTHER INFORMATION: primer

<400> SEQUENCE: 8
```

```
ctagaattct cagcacggag tggcct                                    26

<210> SEQ ID NO 9
<211> LENGTH: 24
<212> TYPE: DNA
<213> ORGANISM: artificial
<220> FEATURE:
<223> OTHER INFORMATION: primer

<400> SEQUENCE: 9
atagctagcg cgaccgtccc cgcc                                      24

<210> SEQ ID NO 10
<211> LENGTH: 26
<212> TYPE: DNA
<213> ORGANISM: artificial
<220> FEATURE:
<223> OTHER INFORMATION: primer

<400> SEQUENCE: 10
ctggaattct catgagtccg cgcgcc                                    26
```

LINCOSAMIDE DERIVATIVES, PREPARATION AND USE THEREOF AS ANTIMICROBIAL AGENT

FIELD OF ART

The present invention relates to novel hybrid lincosamides, their preparation using the enzymatic activities from celesticetin biosynthesis, and their use as antimicrobial agents.

BACKGROUND ART

Lincosamides are a small group of natural substances. Apart from by-products of cultivation, only three natural lincosamide compounds have been described so far. The basic structure of lincosamides is formed by an amino acid unit, a proline derivative, and a sugar moiety which is an unusual amino octose, interconnected by an amide bond. The general formula and substituents corresponding to the three natural lincosamide compounds are listed below. The structurally simplest natural lincosamide is Bu-2545 ($R_1$=H; $R_2$=$CH_3$; $R_3$=O—$CH_3$). A biosynthetically more complex natural substance is lincomycin with a propyl side chain in the 4' position of the proline unit ($R_1$=$C_3H_7$; $R_2$=$CH_3$; $R_3$=OH). The third natural lincosamide substance, celesticetin, lacks the alkyl side chain of the amino acid unit ($R_1$=H), and compared to lincomycin, it contains two additional modifications to the aminosaccharide (sugar) unit: O-methylation at position 7 (similar to Bu-2545) and a salicylate unit bound by the two-carbon linker to the sulphur atom ($R_2$=$CH_2$—$CH_2$-salicylate; $R_3$=O—$CH_3$).

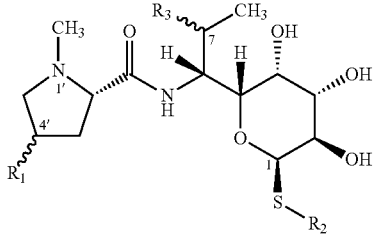

Bu-2545: $R_1$=H, $R_2$=$CH_3$, $R_3$=$OCH_3$ (R configuration)
Lincomycin: $R_1$=$C_3H_7$ (R configuration), $R_2$=$CH_3$, $R_3$=OH (R configuration)
Celesticetin: $R_1$=H, $R_2$=

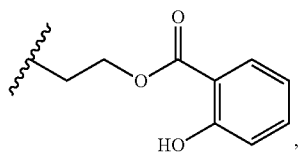 [SMILES: *CCOC(=O)c1ccccc1O]

$R_3$=$OCH_3$ (R configuration)

Natural lincosamides have antibacterial activity. However, only the most effective of them, lincomycin, is industrially manufactured and medically used directly as an antibiotic. Furthermore, its chlorination produces a semi-synthetic derivative, clindamycin ($R_3$=Cl, S configuration), the most efficient lincosamide substance produced. It is primarily used as an antibacterial agent, but, due to its antiprotozoal activity, it is also used as an antimalarial drug.

Many lincomycin derivatives chemically modified on both the amino acid and the sugar units, some more effective than lincomycin and even clindamycin, have been tested. Thus, in the basic structure of lincomycin, three positions have previously been identified, the modifications of which affect activity: In addition to position 7 of the sugar unit, the chlorination of which yields clindamycin, it is the position 4' of the proline unit where longer alkyl side chains than the propyl present in lincomycin, in particular 4-6 carbon long, significantly increase the antibacterial activity of the respective substances. In combination with chlorination at position 7, these compounds also show significant antiplasmodial effects. Antibacterial and antimalarial effects of clindamycin derivatives are further potentiated by the absence of the N-methyl group at position 1'. The most effective derivatives of lincomycin are 1'-demethyl-4'-depropyl-4'-pentyl-clindamycin and 1'-demethyl-4'-depropyl-4'-hexylclindamycin. However, their preparation by chemical synthesis is too complex and their production would thus not be effective.

On the contrary, celesticetin appears to have a low antimicrobial activity, so its derivatives escaped the attention of researchers. Likewise, no hybrid compounds combining the aforementioned specific modifications of lincomycin ($R_1$=alkyl) and celesticetin ($R_2$=$CH_2$—$CH_2$-salicylate) were prepared or tested. Logically it was considered unpractical to modify the more active lincomycin on the sulfur atom bound in the position 1 of the sugar unit by the substituent $R_2$ specific for less effective celesticetin, including taking into account the considerable difficulty of preparing such a hybrid substance by chemical synthesis.

There is still a need to look for new lincosamide compounds that combine high antimicrobial activity with a simple and economically acceptable preparation.

DISCLOSURE OF THE INVENTION

The present invention provides novel lincosamides combining at the same time substitution with an alkyl in the 4' position of the proline unit and ornamentation of the glycosidically bound sulfur atom by a two-carbon alkyl with an ester-linked benzoic acid or derivative thereof. No hybrid lincosamide compounds combining celesticetin-specific modifications ($CH_2$—$CH_2$-salicylate such as $R_2$) and lincomycin (propyl side chain as $R_1$) have not yet been prepared or tested. Surprisingly and contrary to the present general knowledge, this combination of substitutions leads to an increase in antimicrobial activity. The production of hybrid substances modified simultaneously at positions 4' and 1 by chemical synthesis would be extremely demanding. The present invention provides an enzymatic pathway. Thus, an effective preparation of these compounds is disclosed, using enzymatically catalyzed processes based on new knowledge about the mechanism of enzyme functions involved in the natural celesticetin biosynthesis obtained by the inventors in the framework of the present invention.

Object of the present invention are compounds of general formula I

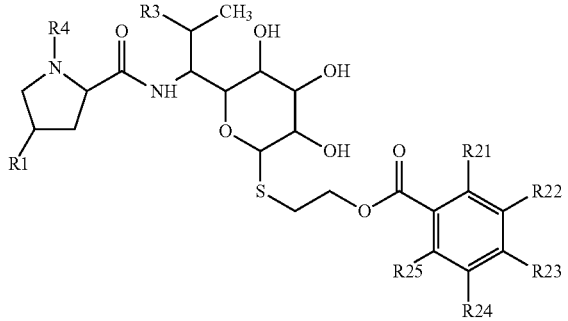

(I)

wherein
R1 is selected from C2-C8 alkyls or C2-C8 alkenyls;
R3 is selected from OH, O(C1-C4 alkyl), SH, S(C1-C4 alkyl) or halogen; preferably OH, O(C1-C2 alkyl), SH, S(C1-C2 alkyl) or halogen;
R4 is H or C1-C3 alkyl; preferably H or C1-C2 alkyl;
each of R21, R22, R23, R24, R25 is independently selected from the group consisting of H, OH, C1-C4 alkyl, C1-C4 alkenyl, C1-C4 alkynyl, halogen, O(C1-C4 alkyl), O(C1-C4 alkenyl), O(C1-C4 alkynyl), $NH_2$, N(C1-C4 alkyl)$_2$, N(C1-C4 alkenyl)$_2$, N(C1-C4 alkynyl)$_2$; preferably H, OH, C1-C2 alkyl, halogen, O(C1-C2 alkyl), $NH_2$, N(C1-C2 alkyl)$_2$;
and pharmaceutically acceptable salts thereof.
Halogens are F, Cl, Br, I. Most preferable halogen is Cl.
R1 is a linear or branched C2-C8 alkyl or C2-C8 alkenyl. Preferably, R1 is a linear or branched C2-C8 alkyl. More preferably, R1 is a linear C2-C8 alkyl. Even more preferably, R1 is C3-C6 alkyl. Most preferably, R1 is selected from the group consisting of propyl, butyl, pentyl, hexyl.
R3 is preferably OH, $OCH_3$, $OCH_2CH_3$ or Cl.
R4 is preferably H or $CH_3$.
Each of R21, R22, R23, R24, R25 is preferably independently selected from the group consisting of H, OH, $CH_3$, $CH_2CH_3$, Cl, Br, I, $OCH_3$, $OCH_2CH_3$, $NH_2$.
Preferably, R21 is selected from the group consisting of OH, $CH_3$, $CH_2CH_3$, Cl, Br, I, $OCH_3$, $OCH_2CH_3$, $NH_2$, H.
Preferably, R22 is selected from the group consisting of H, OH, $NH_2$, Cl.
Preferably, R23 is selected from the group consisting of OH, $CH_3$, $CH_2CH_3$, Cl, Br, I, $OCH_3$, $OCH_2CH_3$, $NH_2$, H.
Preferably, R24 is selected from the group consisting of H, OH, $NH_2$, Cl.
Preferably, R25 is selected from the group consisting of OH, $CH_3$, $CH_2CH_3$, Cl, Br, I, $OCH_3$, $OCH_2CH_3$, $NH_2$, H.
Most preferably, R25 is OH and R21, R22, R23, R24 are H.
Further preferred combinations of substituents R21 to R25 are listed in the following table:

| R21 | R22 | R23 | R24 | R25 |
|---|---|---|---|---|
| H | H | H | H | $NH_2$ |
| H | H | H | H | $CH_3$ |
| H | H | H | H | Cl |
| H | H | H | H | Br |
| H | H | H | H | I |
| H | H | H | H | $OCH_3$ |
| H | H | H | H | H |
| H | H | H | OH | H |
| H | H | H | $NH_2$ | H |
| H | H | H | Cl | H |
| H | H | OH | H | H |
| H | H | $NH_2$ | H | H |
| H | H | $CH_3$ | H | H |
| H | H | Cl | H | H |
| OH | H | H | H | OH |
| H | H | OH | H | OH |
| H | H | $NH_2$ | H | OH |
| H | H | $NH_2$ | H | Cl |
| H | H | Cl | H | Cl |
| H | H | OH | OH | H |
| H | H | Cl | Cl | H |
| H | OH | H | OH | H |
| H | Cl | H | Cl | H |
| H | OH | H | H | OH |
| H | OH | OH | OH | H |
| H | H | Cl | OH | H |
| H | H | OH | Cl | H |
| H | Cl | H | OH | H |

Pharmaceutically acceptable acids suitable for forming the pharmaceutically acceptable addition salts of the compounds of general formula I are in particular 1-hydroxynaphthalene-2-carboxylic acid, 2,2-dichloroacetic acid, 2-hydroxyethanesulphonic acid, 2-oxoglutaric acid, 4-acetamidobenzoic acid, 4-aminosalicylic acid, acetic acid, adipic acid, ascorbic acid, aspartic acid, benzenesulphonic acid, benzoic acid, hydrochloric acid, camphoric acid, camphor-10-sulphonic acid, decanoic acid, hexanoic acid, octanoic acid, carbonic acid, cinnamic acid, citric acid, cyclamic acid, dodecylsulphuric acid, ethane-1,2-disulphonic acid, ethanesulphonic acid, formic acid, fumaric acid, galactaric acid, gentisic acid, glucoheptanoic acid, gluconic acid, glucuronic acid, glutamic acid, glutaric acid, glycerophosphoric acid, glycolic acid, hippuric acid, hydrobromic acid, isobutanoic acid, lactic acid, lactobionic acid, lauric acid, maleinic acid, malonic acid, malic acid, mandelic acid, methanesulphonic acid, naphthalene-1,5-disulphonic acid, naphthalene-2-sulphonic acid, nicotinic acid, nitric acid, oleic acid, oxalic acid, palmitic acid, pamoic acid, phosphoric acid, propanoic acid, pyroglutamic acid, salicylic acid, sebacic acid, stearic acid, succinic acid, sulphuric acid, tartaric acid, thicyanic acid, toluenesulphonic acid, undecylenic acid (P. H. Stahl and C. G. Wermuth, editors, *Handbook of Pharmaceutical Salts: Properties, Selection and Use*, Weinheim/Zürich: Wiley-VCH/VHCA, 2002).

Preferably, the general formula I has the following configurations at chiral centers:

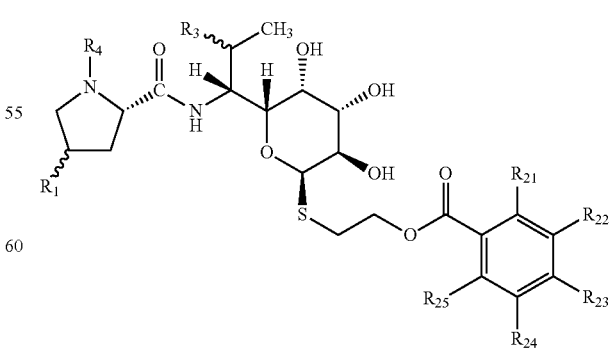

Chiral centers binding groups R1 and R3 may have both R and S configurations (all four possible combinations).

More preferably, the chiral center binding group R1 has the configuration R. More preferably, the chiral center binding group R3 has the configuration R, when R3=OH, OCH$_3$, OCH$_2$CH$_3$, or the configuration S, when R3=halogen. Particularly, the chiral center binding group R3 preferably has the configuration S, when R3=chloro.

Most preferably, the novel lincosamides have the structure:

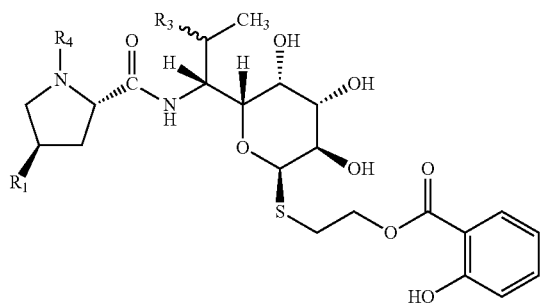

wherein R1=propyl or butyl or pentyl or hexyl, R3=OH (configuration R) or OCH$_3$ (configuration R) or Cl (configuration S), R4=H or CH$_3$.

The present invention further provides a process for the preparation of compounds of formula I which comprises the step of enzymatically catalysed activation of a R21-, R22-, R23-, R24-, R25-substituted benzoic acid derivative by coenzyme A attachment and a step of enzymatically catalyzed esterification of a precursor of formula II

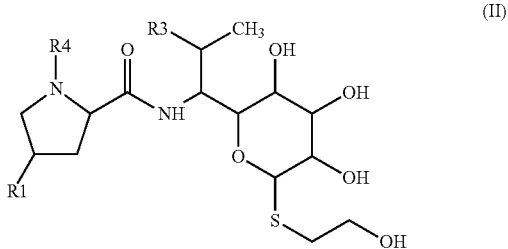

with a conjugate of coenzyme A and R21-, R22-, R23-, R24- and, R25-substituted benzoic acid derivative.

The substituents R1, R3, R4 are as defined in formula (I).

Compounds bearing R3=halogen are obtained from products of the enzymatically catalyzed reaction by known synthetic halogenation methods, e.g., compounds bearing R3=Cl can be obtained by chlorination methods used in clindamycin production.

Compounds bearing R1 being longer than C$_3$H$_7$ may be obtained analogically to a published (Ulanova D., et al. (2010) *Antimicrob. Agents Chemother.* 54(2), 927) and patented (WO2010127645) procedure for preparation of 4'-butyl-4'-depropyllincomycin a 4'-depropyl-4'-pentyllincomycin.

A protein containing the celesticetin biosynthetic protein Ccb2 whose amino acid sequence is disclosed in the GenBank database under accession No. ADB92576 or containing Ccb2-like protein having at least 95% identity with the amino acid sequence of Ccb2 (the 5% difference may generally include chain extension or truncation, or point amino acid mutation) may preferably be used as the enzyme for the enzymatically catalysed activation of a R21-, R22-, R23-, R24-, and R25-substituted benzoic acid derivative by coenzyme A attachment. In addition to the Ccb2 or Ccb2-like protein, the protein may further contain, for example, a tag or another sequence which is not essential for the enzymatic activity.

A protein containing the celesticetin biosynthetic protein Ccb1 whose amino acid sequence is disclosed in the GenBank database under accession No. ADB92559 or containing Ccb1-like protein having at least 95% identity with the amino acid sequence of Ccb1 (the 5% difference may generally include chain extension or truncation, or point amino acid mutation) may preferably be used as the enzyme for the esterification of the precursor of formula II. In addition to the Ccb1 or Ccb1-like protein, the protein may further contain, for example, a tag or another sequence which is not essential for the enzymatic activity.

Thus, an effective preparation of the novel compounds of formula I is enabled by the use of enzyme-catalyzed processes based on new knowledge of the properties of the enzymes involved in the natural celesticetin biosynthesis, namely of a pair of enzymes which catalyze the attachment of the salicylate unit: Ccb2 which activates salicylate by the addition of coenzyme A and, in particular, Ccb1, an acyltransferase catalyzing the attachment (esterification) of the activated salicylate to the sugar unit of the antibiotic through the S—CH$_2$—CH$_2$—OH linker (corresponding to the esterification of the activated benzoic acid derivative and the precursor of formula II). These novel data about the enzymes Ccb2 and Ccb1 have been obtained by the inventors in the framework of the present invention, and the broad substrate specificity of the enzymes to both substrates of the esterification reaction (activated benzoic acid derivatives and precursors of the formula II) is documented in the Examples section, and its use for the enzymatic preparation of lincosamides 1-120 of formula I is shown.

Preferably, the reaction mixture comprises Ccb2, Ccb1, a benzoic acid derivative bearing R21 to R25, adenosine triphosphate, coenzyme A, MgCl$_2$, and a buffer having the pH within the range of 6 to 9 (preferably Tris buffer, pH 7.5). The reaction mixture is preincubated at a temperature in the range of 20 to 40° C., preferably 24 to 34° C., for 15 to 60 minutes, preferably 25 to 40 minutes, then the precursor of formula II is added and the mixture is incubated at a temperature in the same range for 1 to 3 hours. Lincosamides of formula I can be isolated from the mixture by protein precipitation (preferably by formic acid), centrifugation, supernatant extraction, and isolation from the extract by chromatographic separation. A reverse stationary phase (preferably C18 ligand) chromatography column and a gradient separation with a mobile phase having an acidic or neutral pH of the aqueous component (preferably a solution of formic acid in combination with an organic modifier, e.g., methanol or acetonitrile) is suitable.

The precursor of general formula II can be obtained by known procedures, e.g. by enzymatic transformation of the precursor of general formula III.

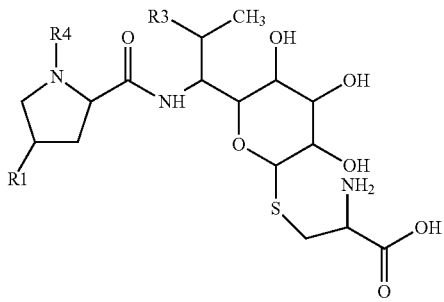

(III)

Preferably, proteins containing celesticetin biosynthetic proteins: CcbF, the amino acid sequence of which is published in the GenBank database under Accession No. ADB92565, or a CcbF-like protein having at least 95% identity with the CcbF amino acid sequence (the 5% difference may generally include chain extension or truncation, or point amino acid mutation); Ccb5, the amino acid sequence of which is published in the GenBank database under accession number ADB92579, or a Ccb5-like protein with at least 95% identity with the Ccb5 amino acid sequence (the 5% difference may generally include chain extension or truncation, or point amino acid mutation); and optionally Ccb4, the amino acid sequence of which is published in the GenBank database under accession number ADB92578, or a Ccb4-like protein with at least 95% identity with the Ccb4 amino acid sequence (the 5% difference may generally include chain extension or truncation, or point amino acid mutation). CcbF, Ccb5 and Ccb4 were described in Kamenik, Z., et al. (2016) *Chem. Sci.*, 7(1), 430-435; Wang, M., et al. (2016) *J. Am. Chem. Soc.*, 138(20), 6348-6351.

Preferably, the reaction mixture contains CcbF, Ccb5, precursor of formula III and pyridoxal-5-phosphate, and a buffer having the pH within 6 to 9 (preferably Tris buffer, pH 7.5). When R3 should be $OCH_3$, then Ccb4 and S-adenosylmethionine are also present in the reaction mixture. The reaction mixture is then incubated at a temperature in the range of 20 to 40° C., preferably 24 to 34° C., for 1 to 4 hours, preferably 90 to 150 minutes.

The substituents R1, R3, R4 in formula III can be as defined for formula I.

In one preferred embodiment, the enzymatically catalyzed activation of the R21-, R22-, R23-, R24-, and R25-substituted benzoic acid derivative by coenzyme A attachment, and the enzymatically catalyzed esterification of the precursor of formula II by the conjugate of the coenzyme A with benzoic acid derivative substituted by R21, R22, R23, R24 and R25, are performed biosynthetically using a microorganism bearing coding sequences of the celesticetin biosynthesis proteins Ccb1 and/or Ccb2, or of biosynthetic proteins having 95% identity with the amino acid sequences of Ccb1 and Ccb2.

Preferably, such microorganism is a microorganism of the class Actinobacteria, preferably of the genus *Streptomyces*.

Preferably, the microorganism bears the coding sequences of the celesticetin biosynthetic proteins Ccb1, Ccb2, Ccb5, CcbF, and when R3 is $OCH_3$, then also Ccb4, or of biosynthetic proteins having 95% identity with the amino acid sequences of Ccb1, Ccb2, Ccb5, CcbF, optionally also Ccb4, and the method starts from the precursor of formula III.

More preferably, the microorganism further bears also coding sequences of the proteins controlling the biosynthesis of the precursor of the formula III, i.e., the respective genes of the lincomycin and/or celesticetin biosynthetic cluster of genes. Biosynthetic gene clusters are described in the literature and their nucleotide sequences are published in the GenBank database, specifically for lincomycin (Koberska, M., et al. (2008) *Folia Microbiol.*, 53(5), 395-401; GenBank EU124663) and for celesticetin (Janata, J., et al. (2015) *PloS One*, 10(3), e0118850; GenBank GQ844764). From the literature, the biosynthetic relevance of individual genes for the production of particular precursor III variants differing in R1, R3 and R4 is known (further to the above-cited literature, also Kamenik, Z., et al. (2016) *Chem. Sci.*, 7(1), 430-435; Jiraskova P., et al. (2016) *Front. Microbiol.*, 7, 276; Najmanova, L., et al. (2013) *ChemBioChem*, 14(7), 2259).

A process for the preparation of lincosamide compounds of formula I with an R1 alkyl longer than $C_3H_7$ may be based on a precursor of formula III in which R1 is already an extended alkyl. Such a precursor may preferably be obtained by supplementing the culture medium of the microorganism producing precursor of formula III wherein $R1=C_3H_7$ with a synthetically prepared 4-alkyl-L-proline wherein the length of this 4-alkyl corresponds to the alkyl length at the R1 position of the desired precursor of formula III. The preparation of synthetic 4-alkyl-L-prolines and their use for the preparation of derivatives of lincomycin with R1 longer than $C_3H_7$ is described in the literature (Ulanova D., et al. (2010) *Antimicrob. Agents Chemother.* 54(2), 927); patent WO2010127645).

All compounds obtained by the above processes may be further modified, if needed, by synthetic procedures well known to those skilled in the art, for example, by chlorination at C-7 of the sugar moiety (to form R3=Cl).

The present invention further relates to genetically modified production microorganisms of the class Actinobacteria, preferably of the genus *Streptomyces*, carrying the coding sequences of the celesticetin biosynthetic proteins Ccb1 and/or Ccb2, or biosynthetic proteins having at least 95% identity of the amino acid sequence with Ccb1 or Ccb2, respectively, and preferably also carrying the coding sequences of the proteins controlling biosynthesis of the precursor of the formula II, i.e. the respective genes of the lincomycin and/or celesticetin biosynthetic cluster of genes. Biosynthetic gene clusters are described in the literature and their nucleotide sequences are published in the GenBank database, specifically for lincomycin (Koberska, M., et al. (2008) *Folia Microbiol.*, 53(5), 395-401; GenBank EU124663); and for celesticetin (Janata, J., et al. (2015) *PloS One*, 10(3), e0118850; GenBank GQ844764). From the literature, the biosynthetic relevance of the individual genes to the production of particular precursor II variants differing in R1, R3 and R4 is known (further to the above-cited literature, also Kamenik, Z., et al. (2016) *Chem. Sci.*, 7(1), 430-435; Jiraskova P., et al. (2016) *Front. Microbiol.*, 7, 276; Najmanova, L., et al. (2013) *ChemBioChem*, 14 (7), 2259).

The present invention further relates to genetically modified production microorganisms of the class Actinobacteria, preferably of the genus *Streptomyces*, carrying the coding sequences of the celesticetin biosynthetic proteins Ccb1, Ccb2, Ccb5, CcbF, and when the produced lincosamides should have $R3=OCH_3$, then also of Ccb4, or of biosynthetic proteins having at least 95% identity of the amino acid sequence with Ccb1, Ccb2, Ccb5, CcbF, optionally also Ccb4, and preferably also carrying the coding sequences of the proteins controlling biosynthesis of the precursor of the formula III, i.e. the respective genes of the lincomycin and/or celesticetin biosynthetic cluster of genes. Biosynthetic gene clusters are described in the literature and their nucleotide sequences are published in the GenBank database, specifically for lincomycin (Koberska, M., et al. (2008) *Folia Microbiol.*, 53(5), 395-401; GenBank EU124663); and for celesticetin (Janata, J., et al. (2015) *PloS One*, 10(3), e0118850; GenBank GQ844764). From the literature, the biosynthetic relevance of the individual genes to the production of particular precursor III variants differing in R1, R3 and R4 is known (further to the above-cited literature, also Kamenik, Z., et al. (2016) *Chem. Sci.*, 7(1), 430-435; Jiraskova P., et al. (2016) *Front. Microbiol.*, 7, 276; Najmanova, L., et al. (2013) *ChemBioChem*, 14 (7), 2259).

In the case of proteins having at least 95% identity with celesticetin biosynthesis proteins, it is understood that the mutations are such that their enzymatic activity is maintained, i.e. they have at least 50% of the enzymatic activity of the respective celesticetin biosynthetic protein. This can be verified by methods known to those skilled in the art.

Furthermore, the present invention provides compounds of formula I for use as pharmaceuticals, especially as antimicrobial drugs. The term "antimicrobial drugs" refers to drugs having effects on unicellular microorganisms such as bacteria and unicellular eukaryotic parasitic microorganisms, in particular on Gram-positive bacteria and parasites of the phylum Apicomplexa comprising target organelles, apicoplasts, especially *Plasmodium, Toxoplasma, Babesia, Theileria* and *Coccidia*.

For therapeutic use, the formulations may be formulated into pharmaceutical compositions which contain mixtures of active compounds of formula I or pharmaceutically acceptable salts thereof with auxiliaries. The auxiliaries include, in particular, solvents such as water, ethanol, propylene glycol, butylene glycol, glycerol, macrogols, oils, isopropyl myristate, benzyl alcohol, ethyl oleate, liquid paraffin, decyl oleate, isopropyl palmitate; ointment and cream bases such as paraffin, petroleum jelly, silicones, fats, waxes, higher aliphatic alcohols and acids, cellulose, cellulose ethers and esters, starch, tragacanth, sodium alginate, talc, zinc, magnesium, titanium oxides, calcium carbonate, magnesium carbonate, colloidal silicon dioxide, aluminum, magnesium, zinc stearates, lactose; fillers such as lactose, native or modified starches, microcrystalline cellulose, mannitol, calcium phosphate, calcium sulfate, sucrose; binders such as starch, gelatin, cellulose and derivatives thereof, e.g., methylcellulose, sodium carboxymethylcellulose, hydroxypropylcellulose, hydroxypropylmethylcellulose, gum arabic, tragacanth, sucrose, glucose, alginic acid and alginates, guar gum, polyvinylpyrrolidone; lubricants such as talc, corn starch, magnesium stearate, colloidal silicon dioxide. Additionally, the auxiliaries may include stabilizers, disintegrants, antioxidants and preservatives. Pharmaceutical compositions may be in particular in the form of tablets, capsules, suppositories, ointments, creams, milk, solutions, or suspensions. The pharmaceutical compositions may further contain, in addition to the active compounds of the formula I, other active substances, in particular antibiotics and antimalarials.

EXAMPLES OF CARRYING OUT THE INVENTION

Example 1: Preparation of a Precursor of Formula III Wherein R1 is C3 Alkyl, R3 is OH, R4 is H or $CH_3$ Cultivation of Streptomycetes in Liquid Medium The culture of the bacterial strain *Streptomyces lincolnensis* ΔlmbIH (construction of this strain of *S. lincolnensis* ATCC 25466 was previously described—Janata, J., et al. (2008) *PLoS One*, 2015, 10, e0118850) was prepared by inoculating spores from a culture dish with MS agar to 50 mL of YEME (Kieser, T., et al (2000) Practical *Streptomyces* Genetics, Norwich, UK, p. 613) medium without sucrose and incubated in 500 mL flat bottom flasks at 28° C. for 120 h. The culture medium was then separated by centrifugation (4000×g, 20° C., 15 min) and the supernatant was used to isolate the lincosamide precursors of formula III in a preferred combination of substituents (R1 is C3 alkyl, R3 is OH, R4 is H or $CH_3$).

Isolation of Lincosamide Precursors of Formula III

Culture medium supernatant was purified using Oasis HLB 6 cc extraction columns (Waters, USA): The supernatant (50 mL) was loaded onto a column preconditioned and equilibrated by methanol (5 mL) and water (5 mL) and a portion of the sample matrix was washed with water (5 mL). Fractions containing lincosamide precursors were eluted with methanol (15 mL), evaporated to dryness and reconstituted in 200 µl of methanol. The obtained extract was reconstituted in 2 mL of methanol and dispensed into a high performance liquid chromatograph (HPLC, Waters, USA) equipped with a gradient pump 600, an autosampler 717 and UV detector 2487 at 194 nm. Data was processed using Empower 2 software (Waters, USA). Lincosamide precursors were separated on a Luna C18 chromatographic column (250×15 mm, particle size 5 µm, Phenomenex, USA) using a two-phase mobile phase, A and B, wherein 0.1% aqueous formic acid (v/v) is used as phase A and methanol as phase B. Chromatographic analyzes using a linear gradient program at a flow rate of 3 mL $min^{-1}$ (min/% B): 0/5, 31/27.5 with subsequent column washing (100% B, 9 min) and equilibration before further analysis (5% B, 9 min). Fractions containing lincosamide precursors were evaporated to dryness, reconstituted in methanol and subjected to further HPLC separation on an XTerra Prep RP18 chromatographic column (150×7.8 mm, particle size 5.0 µm, Waters, USA) using an isocratic elution program at a flow rate of 1.5 mL $min^{-1}$ with 1 mM ammonium formate (pH 9.0): acetonitrile (90:10 v/v) as the mobile phase. Lincosamide precursors isolated in this way were further used for in vitro enzymatic reactions.

Example 2: Preparation of a Precursor of Formula II Wherein R1=C3 Alkyl, R3=OH or $OCH_3$, R4=H or $CH_3$ Heterologous Production and Purification of CcbF, Ccb1, Ccb2, Ccb4 and Ccb5

The CcbF (GenBank ADB92565), Ccb1 (GenBank ADB92559), Ccb2 (GenBank ADB92576), Ccb4 (GenBank ADB92578) and Ccb5 (GenBank ADB92579) proteins for the production of new lincosamide compounds were produced heterologously in *E. coli* cells. The ccbF, ccb1, ccb2, ccb4 and ccb5 genes were PCR amplified using the primers of Table 1 from the genomic DNA of the celesticetin producing strain *Streptomyces caelestis* ATCC 15084. The PCR products were treated with the restriction enzymes (according to Table 1) and inserted into the pET28b (Novagen) vectors for ccb1, ccb4 or ccb5, or pET42b (Novagen) for ccbF or ccb2. The Ccb1, Ccb4 and Ccb5 proteins were thus produced with a N-terminal histidine tag, and the CcbF and Ccb2 proteins were produced with the C-terminal histidine tag. *E. coli* BL21 (DE3) strain carrying the GroES and GroEL chaperonins expression construct was used to produce the proteins. For all recombinant proteins, overproduction was induced by isopropyl β-D-1-thiogalactopyranoside (0.4 mM) at a culture OD (600 nm) of 0.6-0.8. After induction, the culture was incubated at 17° C. at 200 rpm for 20 h. The culture was then centrifuged (4000×g, 20 min, 4° C.) and the sediment was used to prepare the crude extract by ultrasonic homogenization in buffer I (20 mM TRIS pH 8, 100 mM NaCl, 10% glycerol, and 20 mM imidazole). The homogenate was then centrifuged at 9000×g, 25 min, 4° C. The proteins were purified from the crude extract using a 1 mL HiTrap™ $Ni^{2+}$ column according to the manufacturer's protocol (GE Healthcare). The protein Ccb2 was eluted with buffer II (20 mM TRIS pH 8, 100 mM NaCl, 10% glycerol, and 100 mM imidazole), Ccb4 and Ccb5 proteins were eluted with buffer III (20 mM TRIS pH 8, 100 mM NaCl, 10% glycerol, and 200 mM imidazole) and the CcbF and Ccb1 proteins were eluted with buffer IV (20 mM TRIS pH 8, 100 mM NaCl, 10% glycerol, and 250 mM imidazole). Imidazole was removed from the purified protein solution using Amicon centrifuge tubes (Millipore) and buffer V (20 mM TRIS pH 8, 100 mM NaCl, 10% glycerol). All of the proteins thus prepared were stable without loss of activity at 4° C. for at least one week; the CcbF, Ccb1, Ccb2, and Ccb5 proteins were also stable for at least one month at −80° C.

extracted with Oasis HLB 6 cc columns according to the protocol described above in the section of Isolation of lincosamide precursors. The extract was further subjected to HPLC separation as defined in the above paragraph Isolation of lincosamide precursors. New lincosamide compounds were separated on a Luna C18 chromatographic column (250×15 mm, particle size 5 μm, Phenomenex, USA) using a two-phase mobile phase, A and B, wherein 0.1% aqueous formic acid (v/v) was used as the phase A and acetonitrile was used as the phase B. Chromatographic analyses were performed using a linear gradient program at a flow rate of 3 mL min (min/% B): 0/30, 40/65, followed by column washing (100% B, 9 min) and equilibration before further analysis (30% B, 9 min).

Antibacterial Activity Tests

Filtration paper discs (geometric diameter 5 mm) saturated with 5 nmol of tested novel lincosamide compounds were placed on LB agar plates (tryptone 10 g, yeast extract 5 g, NaCl 10 g, supplemented with distilled water to 1000 mL, pH 7.5; agar 15 g) continuously covered with culture of the lincomycin sensitive test strain *Kocuria rhizophila*. The plates were incubated at 37° C. for 20 h.

TABLE 1

Primers used for amplification of the S. caelestis genes. Restriction sites for the insertion into the vector are underlined and following restriction enzymes were used for DNA processing: NdeI for CATATG sequence, XhoI for CTCGAG, EcoRI for GAATTC and NheI for GCTAGC:

| Gene | Primer I | Primer II |
|---|---|---|
| ccbF | CCGCATATGTCCGACTTAGCTGCCG | CCGCTCGAGGCGGGGCTGCCAGGCG |
| ccb1 | CTGCATATGCATCTTGATCCAACCAC | ATAGAATTCTCATCGGTGGTCGTCGC |
| ccb2 | AACCCCATATGAAGCGACGTGGCATGG | AACCCCTCGAGTAAGGTCATGAACTCCGCACG |
| ccb4 | CTACATATGAAGACGCCCGGTACATC | CTAGAATTCTCAGCACGGAGTGGCCT |
| ccb5 | ATAGCTAGCGCGACCGTCCCCGCC | CTGGAATTCTCATGAGTCCGCGCGCC |

In Vitro Enzymatic Preparation of Lincosamide Precursors of Formula II

Reaction mixture 1 contained: 20 μM CcbF, 20 μM Ccb5, 200 μM lincosamide precursor of formula III wherein R1 is C3 alkyl, R3 is OH, R4 is H or $CH_3$, 200 μM pyridoxal-5-phosphate, 100 mM Tris pH 7.5. In the case of the preparation of precursors of formula II wherein R3=$OCH_3$, the reaction mixture additionally contained 20 μM Ccb4 and 4 mM S-adenosylmethionine. Reaction mixture 1 was incubated at 30° C. for 2 h.

Example 3: In Vitro Enzymatic Preparation of New Lincosamide Compounds of Formula I Wherein R1=C3 Alkyl, R3=OH or $OCH_3$ (R Configuration), R4=H or $CH_3$, R21-R24 are H and R25 is OH Reaction mixture 2 contained: 2 μM Ccb2, 2 μM Ccb1, 2 mM salicylic acid, 4.5 mM adenosine triphosphate, 2 mM coenzyme A, 2 mM $MgCl_2$, 100 mM Tris pH 7.5. Reaction mixture 2 was incubated at 30° C. for 30 min. Then, reaction mixture 2 was mixed in a ratio of 1:1 with reaction mixture 1 (preparation according to Example 2) containing the lincosamide precursor of formula II, and incubated at 30° C. for further 2 hours.

Isolation of New Lincosamide Compounds of Formula I from the Enzymatic Reaction Mixture Proteins were precipitated from the reaction mixture with 98% formic acid (30 μL per 1 mL sample) and the mixture was centrifuged (13500 rpm, 5 min). The supernatant was Minimum inhibitory concentrations were determined using the previously published method (European Committee for Antimicrobial Susceptibility Testing (EUCAST), Clin Microbiol Infect (2003), 9 (8), ix-xv). 5 μL suspension (McFarland scale 0.5) of *K. rhizophila* bacterial culture was inoculated into 1 mL of LB medium containing test substances of the desired concentration (a concentration range of 25-1600 nM was tested). The cultures were incubated for 24 h at 37° C.

TABLE 2

Results of biological activity testing

| Tested compound | Disc diffusion test: size of inhibition zones [mm] | Minimum inhibitory concentration [nM] |
|---|---|---|
| Celesticetin | 19 | 1600 |
| Lincomycin | 24 | 400 |
| Compound of formula I, wherein R1 = propyl, R21-R24 = H, R25 = OH, R3 = $OCH_3$, R4 = $CH_3$ | 28 | 100 |
| Compound of formula I, wherein R1 = propyl, R21-R24 = H, R25 = OH, R3 = OH, R4 = $CH_3$ | 29 | 100 |

Analysis by Liquid Chromatography with Mass Spectroscopy Detection (LC-MS Analysis)

In total four lincosamides were prepared: compounds 1-4 with the following structures and LC-MS parameters listed in Table 3.

1

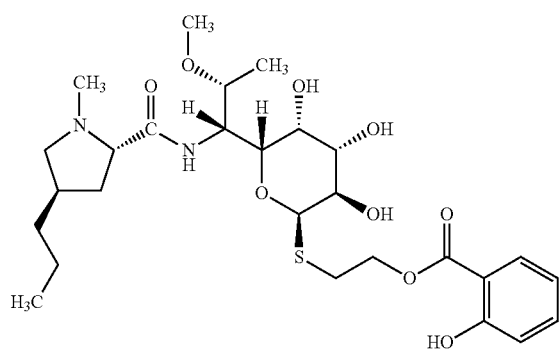

2

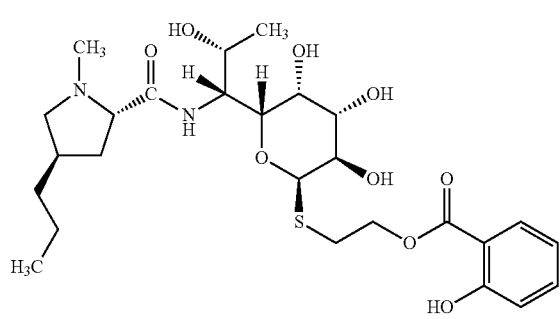

3

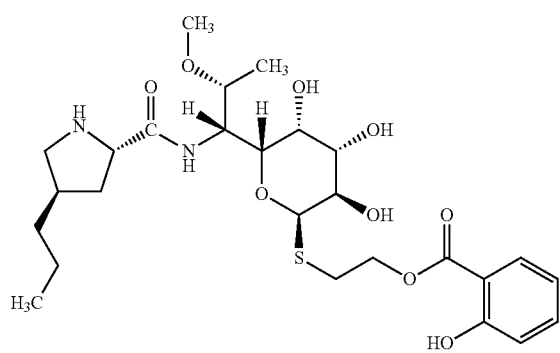

4

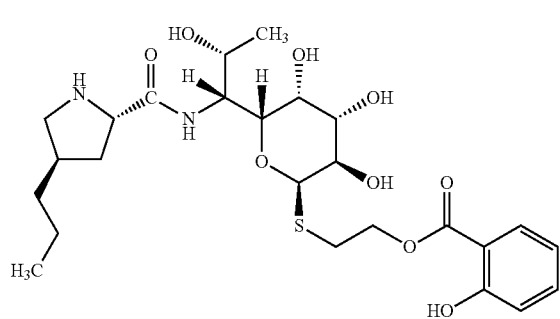

TABLE 3

Results of LC-MS analysis of the compounds 1-4

| Lincosamide | Retention time (min) | Pseudomolecular ion - theoretical value m/z for $z = 1$ | Major detected ion in MS spectrum (m/z) | Fragmentation in source - major detected ions (m/z) |
|---|---|---|---|---|
| 1 | 7.10 | 571.2690 | 571.2703 | 373.23; 126.13 |
| 2 | 6.25 | 557.2533 | 557.2543 | 359.22; 126.13 |
| 3 | 7.00 | 557.2533 | 557.2532 | 359.22; 112.11 |
| 4 | 6.30 | 543.2376 | 543.2358 | 345.20 |

LC-MS analyses were performed on an Ultra High Performance Liquid Chromatograph Acquity UPLC coupled to an LCT premier XE mass spectrometer and a time-of-flight analyzer (Waters, USA). A sample of 5 µl was injected on an Acquity UPLC BEH C18 chromatographic column (50 mm×2.1 mm, particle size 1.7 µm, Waters, USA) which was kept at 40° C. The sample was eluted from the column with two-phase mobile phase, aqueous solution of 0.1% formic acid (v/v) was used as the component A, and acetonitrile was used as the component B. The following linear gradient program (min/% B) 0/5, 1.5/5, 12.5/58 was used for separation at a flow rate of 0.4 mL min$^{-1}$. The analysis included column washing (1.5 min, 100% B) and equilibration before further analysis (1.5 min, 5% B). The mass spectrometer was set to W mode with the following parameters: capillary voltage, +2800 V; cone voltage, +40 V; flow rate of desolvation gas (nitrogen), 800 Lh$^{-1}$; desolvation gas temperature, 350° C.; ion block temperature, 120° C.; cone gas flow rate, 50 Lh$^{-1}$; scan time, 0.15 sec; delay between scans, 0.01 s. The mass accuracy below 5 ppm was maintained with the reference compound leucine-enkephaline (2 ng µL$^{-1}$, 5 µL min$^{-1}$). Source fragmentation (collision initiated dissociation—CID) was induced by increasing aperture I to +50 V. Data were processed using MassLynx V4.1 software (Waters, USA).

Example 4: In Vitro Enzymatic Preparation of Novel Lincosamides of Formula I Wherein R1=C3 Alkyl, R3=OH or OCH$_3$ (R Configuration), R4=H or CH$_3$, R21-R25 are H Reaction mixture 2 contained: 2 µM Ccb2, 2 µM Ccb1, 2 mM benzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (preparation according to Example 2) containing the lincosamide precursor of formula II in a ratio of 1:1 and incubated at 30° C. for further 2 hours. Novel lincosamide with incorporated benzoic acid was isolated from the reaction mixture according to the procedure of Example 3.

Results of LC-MS Analysis

In total four lincosamides were prepared: compounds 5-8 with the following structures and LC-MS parameters listed in Table 4.

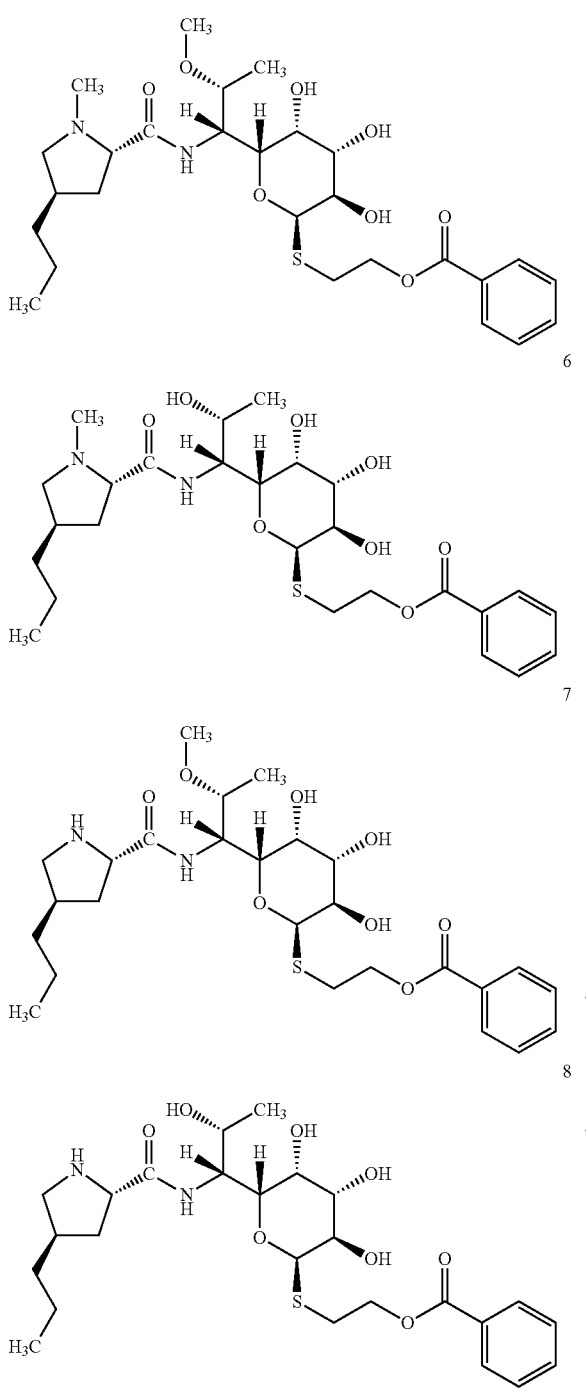

LC-MS analyses were performed according to the procedure described in Example 3.

Example 5: In Vitro Enzymatic Preparation of Novel Lincosamide Compounds of Formula I Wherein R1=C3 Alkyl, R3=OH or OCH₃ (R Configuration), R4=H or CH₃, R21-R24 are H, R25 is NH₂

Reaction mixture 2 contained: 2 µM Ccb2, 2 µM Ccb1, 2 mM anthranilic (2-aminobenzoic) acid, 4.5 mM adenosine triphosphate, 2 mM coenzyme A, 2 mM MgCl₂, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated anthranilic (2-aminobenzoic) acid was isolated from the reaction mixture according to the procedure of Example 3.

LC-MS Analysis

In total four lincosamides were prepared: compounds 9-12 with the following structures and LC-MS parameters listed in Table 5.

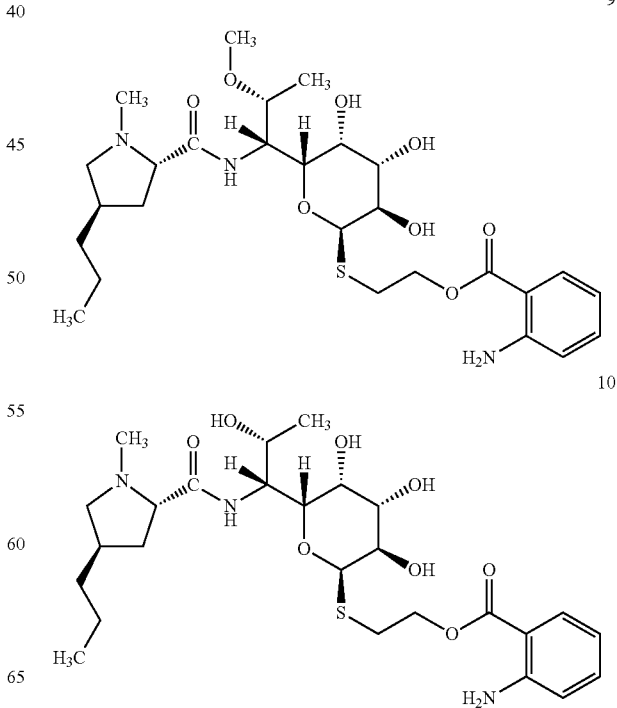

TABLE 4

Results of LC-MS analysis of the compounds 5-8

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 5 | 6.85 | 555.2741 | 555.2743 | 373.23; 126.13 |
| 6 | 6.00 | 541.2584 | 541.2578 | 359.22; 126.13 |
| 7 | 7.00 | 541.2584 | 541.2584 | 359.22; 112.11 |
| 8 | 6.10 | 527.2427 | 527.2424 | 345.20 |

TABLE 5

Results of LC-MS analysis of the compounds 9-12

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 9 | 6.50 | 570.2850 | 570.2842 | 373.23; 126.13 |
| 10 | 5.70 | 556.2393 | 556.2703 | 359.22; 126.13 |
| 11 | 6.50 | 556.2393 | 556.2709 | 359.22; 112.11 |
| 12 | 5.40 | 542.2536 | 542.2548 | 345.20; 112.11 |

LC-MS analyses were performed according to the procedure described in Example 3.

Example 6: In Vitro Enzymatic Preparation of Novel Lincosamide Compounds of Formula I Wherein R1=C3 Alkyl, R3=OCH$_3$ or OH (R Configuration), R4=H or CH$_3$, R21-R24 are H, R25 is CH$_3$ Reaction mixture 2 contained: 2 µM Ccb2, 2 µM Ccb1, 2 mM 2-methylbenzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 2-methylbenzoic acid was isolated from the reaction mixture according to the procedure of Example 3.

LC-MS Analysis

In total four lincosamides were prepared: compounds 13-16 with the following structures and LC-MS parameters listed in Table 6.

TABLE 6

Results of LC-MS analysis of the compounds 13-15

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 13 | 9.00 | 569.2897 | 569.2917 | 373.23; 126.13 |
| 14 | 7.60 | 555.2740 | 555.2742 | 359.22; 126.13 |
| 15 | 8.00 | 555.2740 | 555.2714 | 359.22 |
| 16 | 5.75 | 541.2583 | 541.2570 | 345.20; 112.11 |

LC-MS analyses were performed according to the procedure described in Example 3.

Example 7: In Vitro Enzymatic Preparation of Novel Lincosamide Compounds of Formula I Wherein R1=C3 Alkyl, R3=OH or OCH$_3$ (R Configuration), R4=H or CH$_3$, R21-R24 are H, R25 is Cl Reaction mixture 2 contained: 2 μM Ccb2, 2 μM Ccb1, 2 mM 2-chlorobenzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (preparation according to Example 2) containing the lincosamide precursor of formula II in a ratio of 1:1 and incubated at 30° C. for further 2 hours. The novel lincosamide with incorporated 2-chlorobenzoic acid was isolated from the reaction mixture according to the procedure of Example 3.

LC-MS Analysis

In total, four lincosamides were prepared: compounds 17-20 with the following structures and LC-MS parameters listed in Table 7.

17

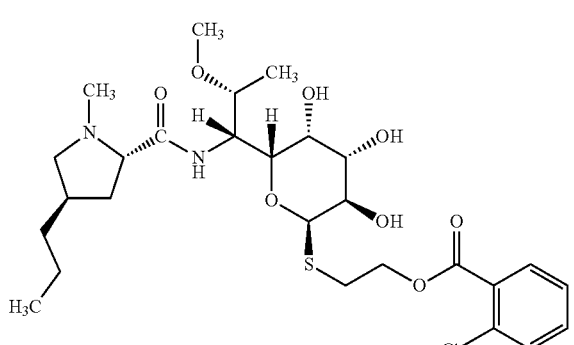

18

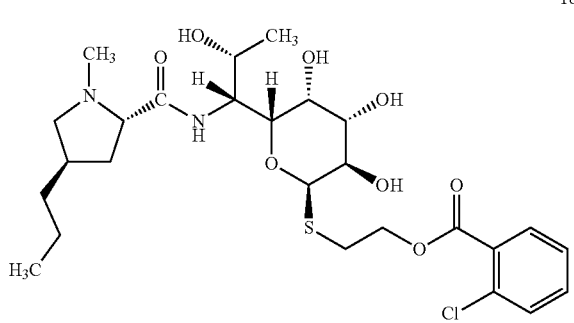

19

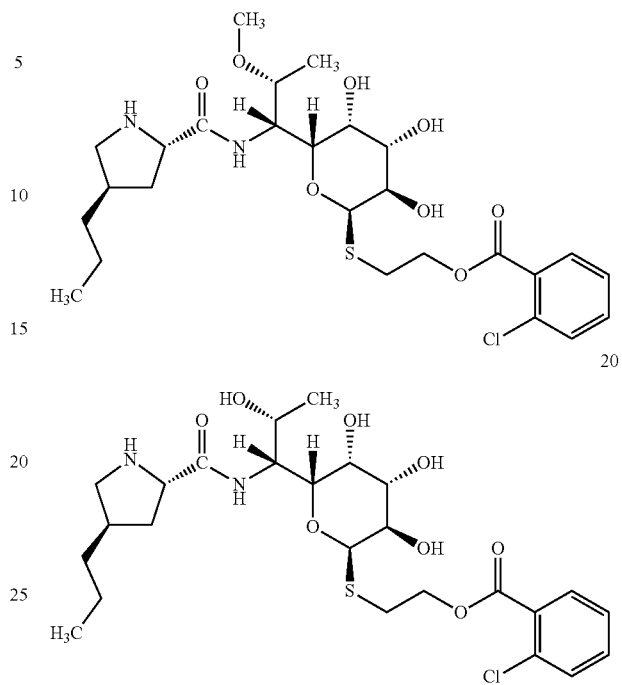

20

TABLE 7

Results of LC-MS analysis of the compounds 17-20

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 17 | 8.63 | 589.2351 | 589.2335 | 373.23; 126.13 |
| 18 | 7.25 | 575.2194 | 575.2183 | 359.22; 126.13 |
| 19 | 6.50 | 575.2194 | 575.2169 | 359.22 |
| 20 | 5.52 | 561.2037 | 561.2045 | 345.20 |

LC-MS analyses were performed according to the procedure described in Example 3.

Example 8: In Vitro Enzymatic Preparation of Novel Lincosamide Compounds of Formula I Wherein R1=C3 Alkyl, R3=OH or OCH$_3$ (R Configuration), R4=H or CH$_3$, R21-R24 are H, R25 is Br Reaction mixture 2 contained: 2 μM Ccb2, 2 μM Ccb1, 2 mM 2-bromobenzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 2-bromobenzoic acid was isolated from the reaction mixture according to the procedure of Example 3.

LC-MS Analysis

In total, four lincosamides were prepared: compounds 21-24 with the following structures and LC-MS parameters listed in Table 8.

21

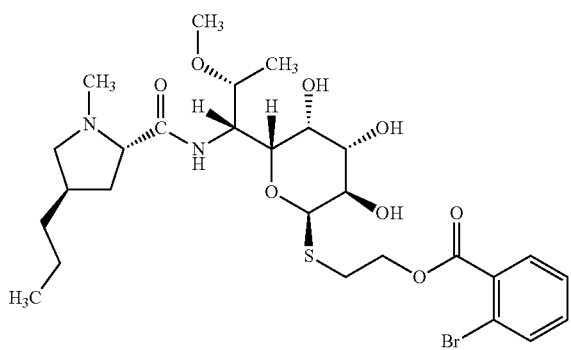

22

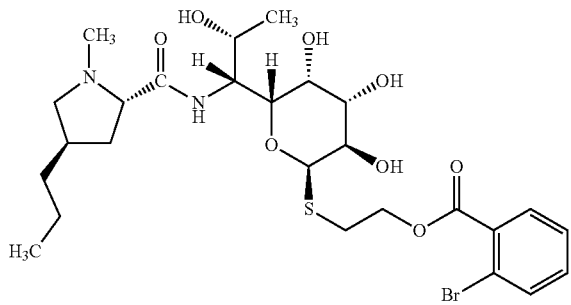

23

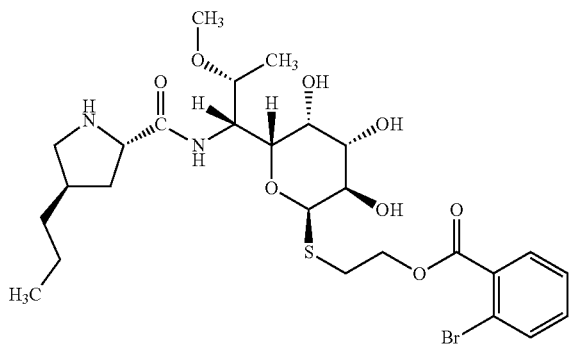

24

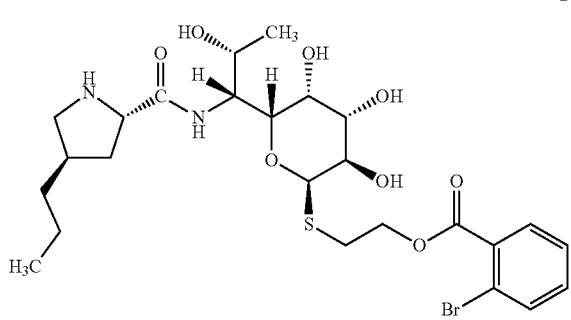

TABLE 8

Results of LC-MS analysis of the compounds 21-24

| Lincosamide | Retention time (min) | Pseudomolecular ion - theoretical value m/z for $z = 1$ | Major detected ion in MS spectrum (m/z) | Fragmentation in source - major detected ions (m/z) |
|---|---|---|---|---|
| 21 | 8.75 | 635.1826 | 635.1833 | 373.24; 126.13 |
| 22 | 7.50 | 621.1669 | 621.1666 | 359.22; 126.13 |
| 23 | 6.63 | 621.1669 | 621.1635 | 359.22 |
| 24 | 5.63 | 607.1511 | 607.1506 | 345.21 |

LC-MS analyses were performed according to the procedure described in Example 3.

Example 9: In Vitro Enzymatic Preparation of Novel Lincosamide Compounds of Formula I Wherein R1=C3 Alkyl, R3=OH or OCH$_3$ (R Configuration), R4=H or CH$_3$, R21-R24 are H, R25 is I Reaction mixture 2 contained: 2 µM Ccb2, 2 µM Ccb1, 2 mM 2-iodobenzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 2-iodobenzoic acid was isolated from the reaction mixture according to the procedure of Example 3.

LC-MS Analysis

In total, four lincosamides were prepared: compounds 25-28 with the following structures and LC-MS parameters listed in Table 9.

25

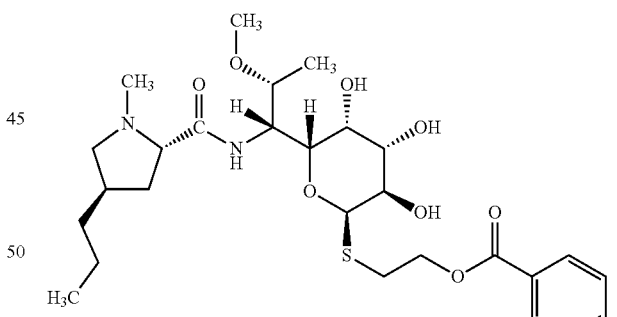

26

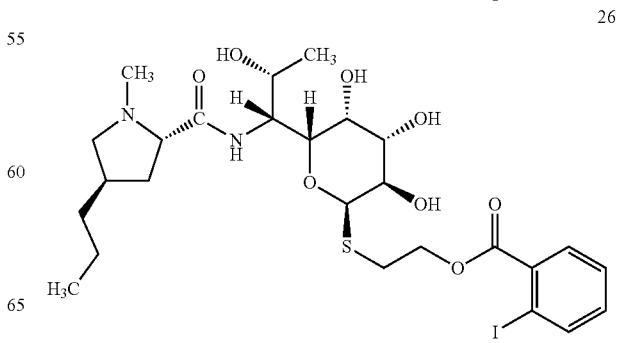

-continued

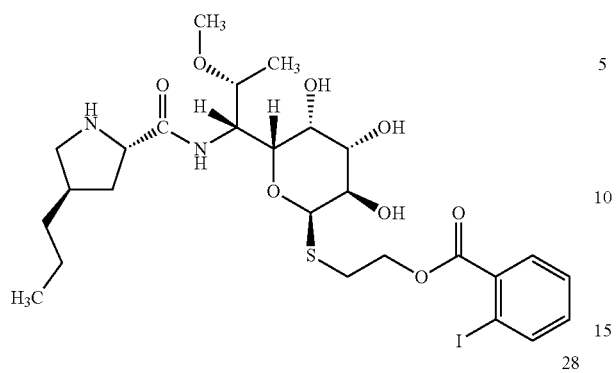

27

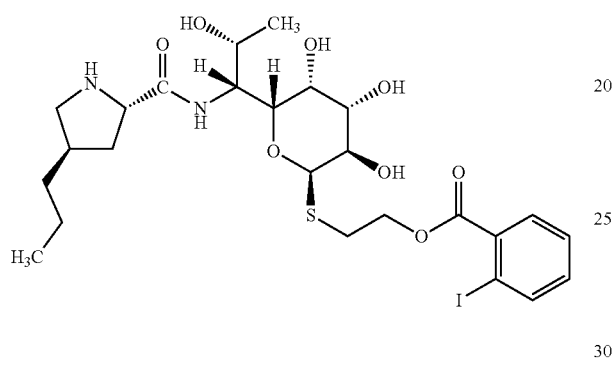

28

TABLE 9

Results of LC-MS analysis of the compounds 25-28

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 25 | 9.13 | 681.1707 | 681.1691 | 373.24; 126.13 |
| 26 | 7.88 | 667.1550 | 667.1524 | 359.22 |
| 27 | 7.00 | 667.1550 | 667.1500 | 359.22 |
| 28 | 5.87 | 653.1393 | 653.1382 | 345.20 |

LC-MS analyses were performed according to the procedure described in Example 3.

Example 10: In Vitro Enzymatic Preparation of Novel Lincosamide Compounds of Formula I Wherein R1=C3 Alkyl, R3=OH or OCH$_3$ (R Configuration), R4=H or CH$_3$, R21-R24 are H, R25 is OCH$_3$ Reaction mixture 2 contained: 2 μM Ccb2, 2 μM Ccb1, 2 mM 2-methoxybenzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 2-methoxybenzoic acid was isolated from the reaction mixture according to the procedure of Example 3.
LC-MS Analysis In total, four lincosamides were prepared: compounds 29-32 with the following structures and LC-MS parameters listed in Table 10.

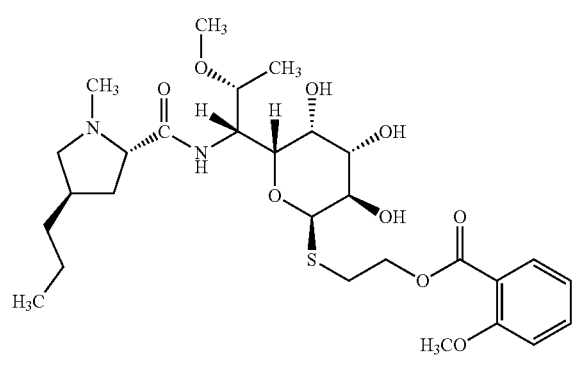

29

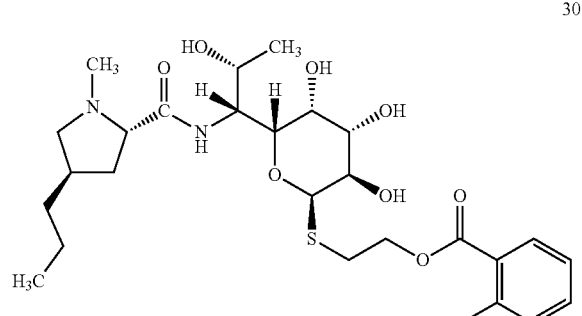

30

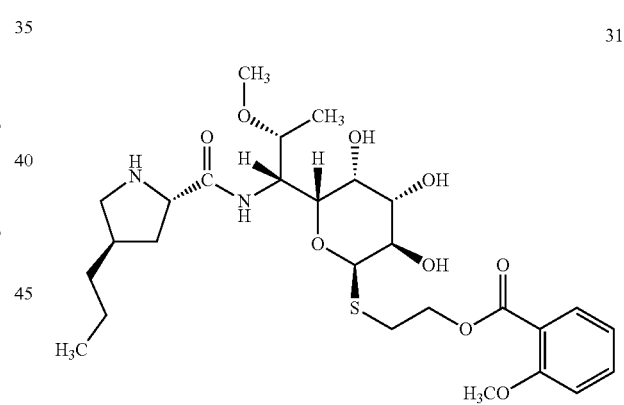

31

32

TABLE 10

Results of LC-MS analysis of the compounds 29-32

| Lincosamide | Retention time (min) | Pseudomolecular ion - theoretical value m/z for $z = 1$ | Major detected ion in MS spectrum (m/z) | Fragmentation in source - major detected ions (m/z) |
|---|---|---|---|---|
| 29 | 7.52 | 585.2846 | 585.2855 | 373.24; 126.13 |
| 30 | 6.36 | 571.2689 | 571.2693 | 359.22 |
| 31 | 5.83 | 571.2689 | 571.2694 | 359.22 |
| 32 | 4.80 | 557.2532 | 557.2521 | 345.20 |

LC-MS analyses were performed according to the procedure described in Example 3.

Example 11: In Vitro Enzymatic Preparation of Novel Lincosamide Compounds of Formula I Wherein R1=C3 Alkyl, R3=OH or OCH$_3$ (R Configuration), R4=H or CH$_3$, R21-R23, R25 are H, R24 is OH Reaction mixture 2 contained: 2 µM Ccb2, 2 µM Ccb1, 2 mM 3-hydroxybenzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 3-hydroxybenzoic acid was isolated from the reaction mixture according to the procedure of Example 3.

LC-MS Analysis

In total, four lincosamides were prepared: compounds 33-36 with the following structures and LC-MS parameters listed in Table 11.

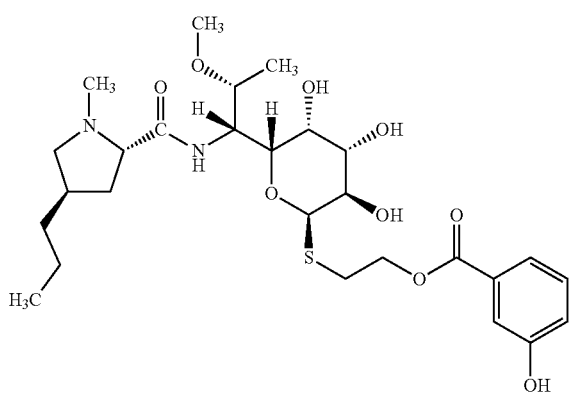

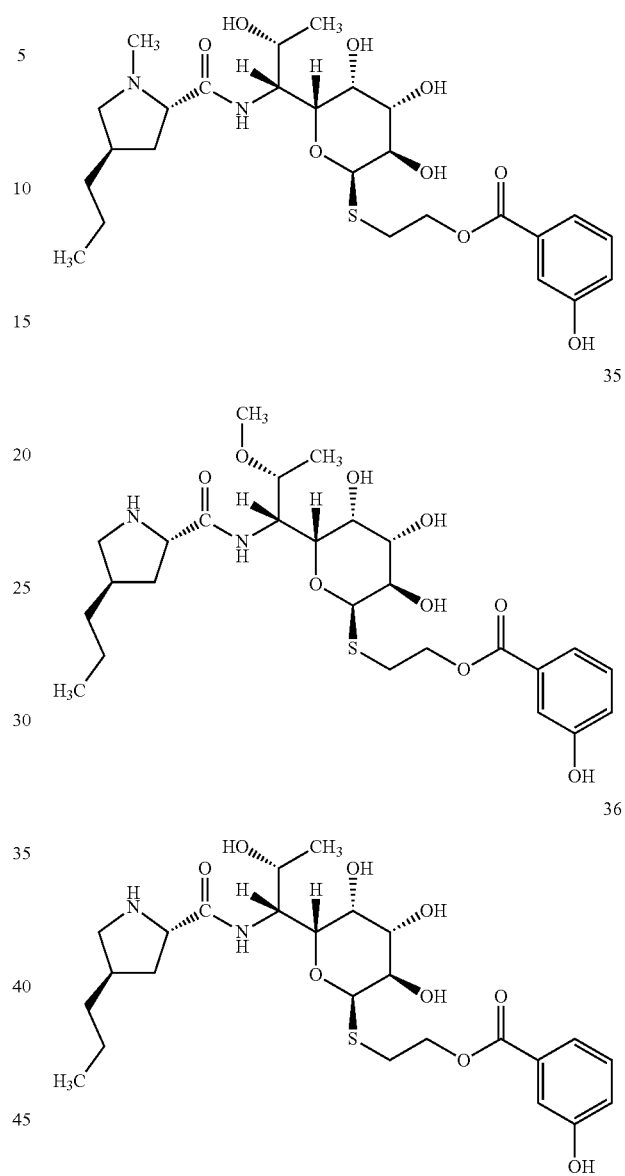

TABLE 11

Results of LC-MS analysis of the compounds 33-36

| Lincosamide | Retention time (min) | Pseudomolecular ion - theoretical value m/z for $z = 1$ | Major detected ion in MS spectrum (m/z) | Fragmentation in source - major detected ions (m/z) |
|---|---|---|---|---|
| 33 | 5.85 | 571.2690 | 571.2688 | 373.24; 126.13 |
| 34 | 5.09 | 557.2533 | 557.2531 | 359.22; 126.13 |
| 35 | 5.92 | 557.2533 | 557.2538 | 359.22 |
| 36 | 5.07 | 543.2376 | 543.2355 | 345.20 |

LC-MS analyses were performed according to the procedure described in Example 3.

Example 12: In Vitro Enzymatic Preparation of Novel Lincosamide Compounds of Formula I Wherein R1=C3 Alkyl, R3=OH or OCH$_3$ (R Configuration), R4=H or CH$_3$, R21-R23, R25 are H, R24 is NH$_2$ Reaction mixture 2 contained: 2 µM Ccb2, 2 µM Ccb1, 2 mM 3-aminobenzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 3-aminobenzoic acid was isolated from the reaction mixture according to the procedure of Example 3.

LC-MS Analysis

In total, four lincosamides were prepared: compounds 37-40 with the following structures and LC-MS parameters listed in Table 12.

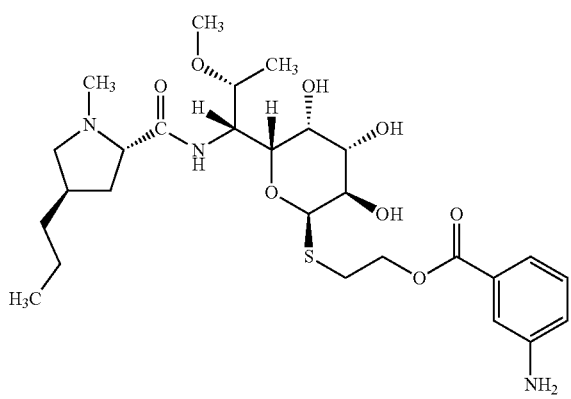

37

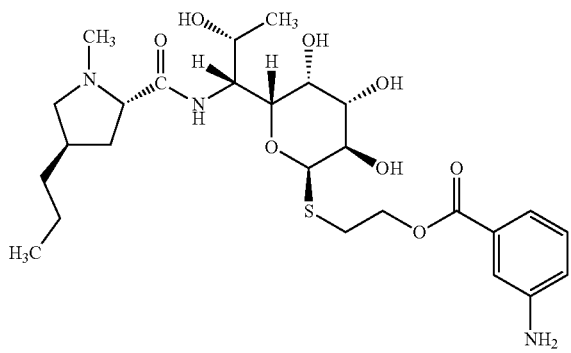

38

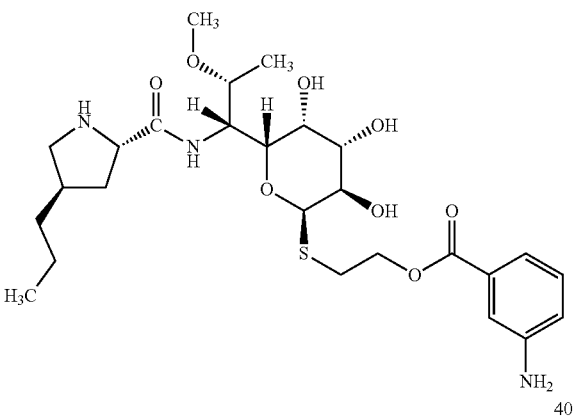

39

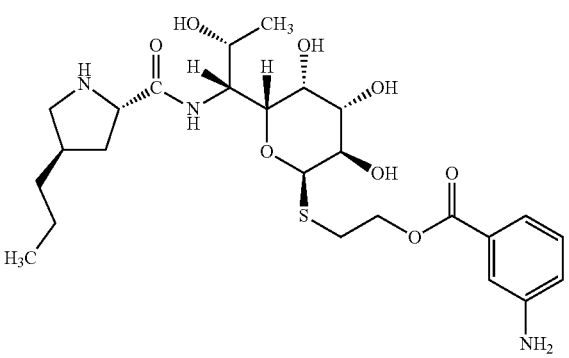

40

TABLE 12

Results of LC-MS analysis of the compounds 37-40

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 37 | 5.35 | 570.2850 | 570.2839 | 373.24; 126.13 |
| 38 | 4.08 | 556.2393 | 556.2684 | 359.20; 126.12 |
| 39 | 5.35 | 556.2393 | 556.2696 | 359.22; 112.11 |
| 40 | 4.13 | 542.2536 | 542.2541 | 345.20 |

LC-MS analyses were performed according to the procedure described in Example 3.

Example 13: In Vitro Enzymatic Preparation of Novel Lincosamide Compounds of Formula I Wherein R1=C3 Alkyl, R3=OH or OCH$_3$ (R Configuration), R4=H or CH$_3$, R21-R23, R25 are H, R24 is Cl Reaction mixture 2 contained: 2 µM Ccb2, 2 µM Ccb1, 2 mM 3-chlorobenzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 3-chlorobenzoic acid was isolated from the reaction mixture according to the procedure of Example 3.

LC-MS Analysis

In total, four lincosamides were prepared: compounds 41-44 with the following structures and LC-MS parameters listed in Table 13.

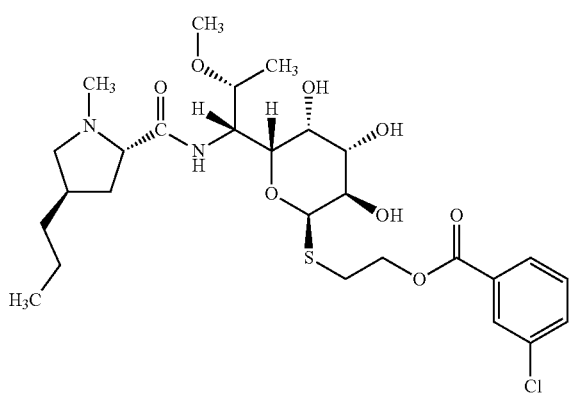

41

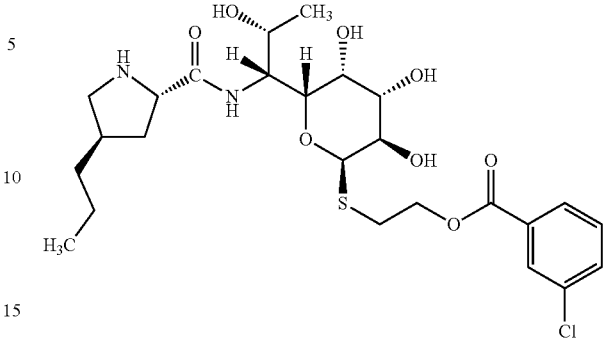

44

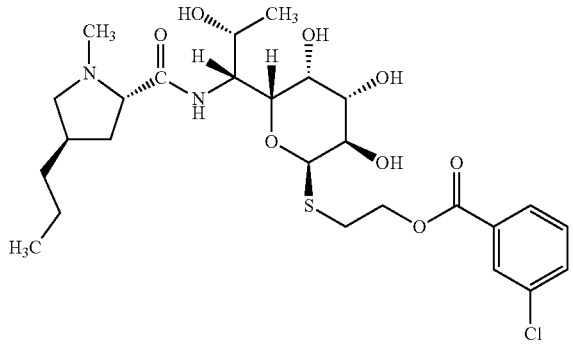

42

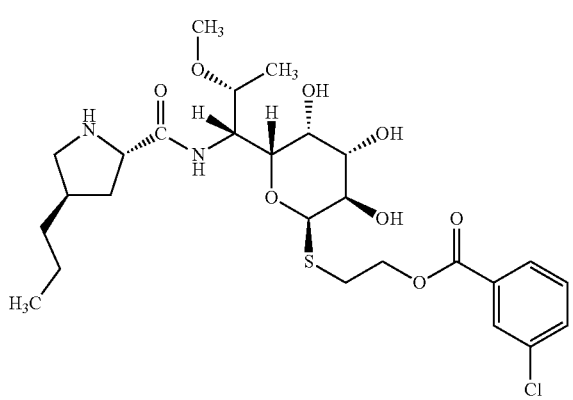

43

TABLE 13

Results of LC-MS analysis of the compounds 41-44

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 41 | 7.20 | 589.2351 | 589.2365 | 373.24; 126.13 |
| 42 | 6.77 | 575.2194 | 575.2185 | 359.22; 126.13 |
| 43 | 7.53 | 575.2194 | 575.2209 | 359.21 |
| 44 | 6.55 | 561.2037 | 561.2030 | 345.21 |

LC-MS analyses were performed according to the procedure described in Example 3.

Example 14: In Vitro Enzymatic Preparation of Novel Lincosamide Compounds of Formula I Wherein R1=C3 Alkyl, R3=OH or OCH$_3$ (R Configuration), R4=H or CH$_3$, R21, R22, R24, R25 are H, R23 is OH Reaction mixture 2 contained: 2 µM Ccb2, 2 µM Ccb1, 2 mM 4-hydroxybenzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 4-hydroxybenzoic acid was isolated from the reaction mixture according to the procedure of Example 3.

LC-MS Analysis

In total, four lincosamides were prepared: compounds 45-48 with the following structures and LC-MS parameters listed in Table 14.

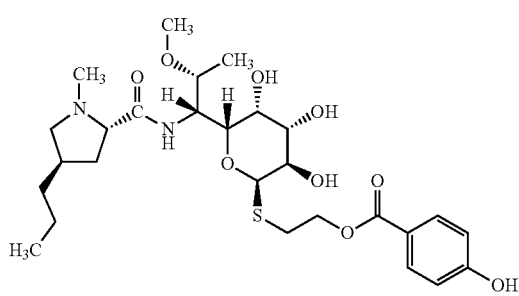

45

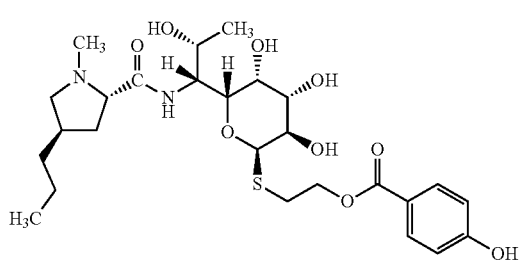

46

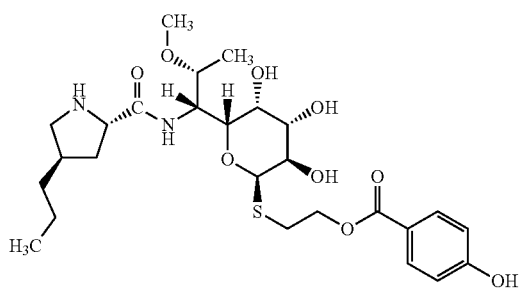

47

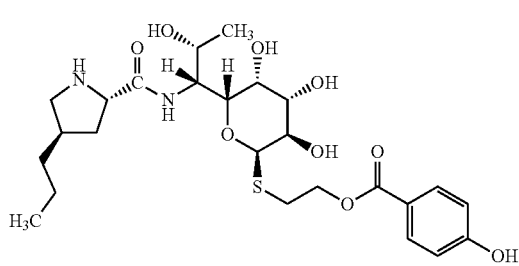

48

TABLE 14

Results of LC-MS analysis of the compounds 45-48

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 45 | 5.76 | 571.2690 | 571.2706 | 373.23; 126.13 |
| 46 | 4.91 | 557.2533 | 557.2551 | 359.22; 126.13 |
| 47 | 5.74 | 557.2533 | 557.2540 | 359.21; 112.11 |
| 48 | 4.97 | 543.2376 | 543.2467 | 345.20 |

LC-MS analyses were performed according to the procedure described in Example 3.

Example 15: In Vitro Enzymatic Preparation of Novel Lincosamide Compounds of Formula I Wherein R1=C3 Alkyl, R3=OH or OCH₃ (R Configuration), R4=H or CH₃, R21, R22, R24, R25 are H, R23 is NH₂

Reaction mixture 2 contained: 2 µM Ccb2, 2 µM Ccb1, 2 mM 4-aminobenzoic acid, 4.5 mM adenosine triphosphate, 2 mM coenzyme A, 2 mM MgCl₂, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 4-aminobenzoic acid was isolated from the reaction mixture according to the procedure of Example 3.

LC-MS Analysis

In total, four lincosamides were prepared: compounds 49-52 with the following structures and LC-MS parameters listed in Table 15.

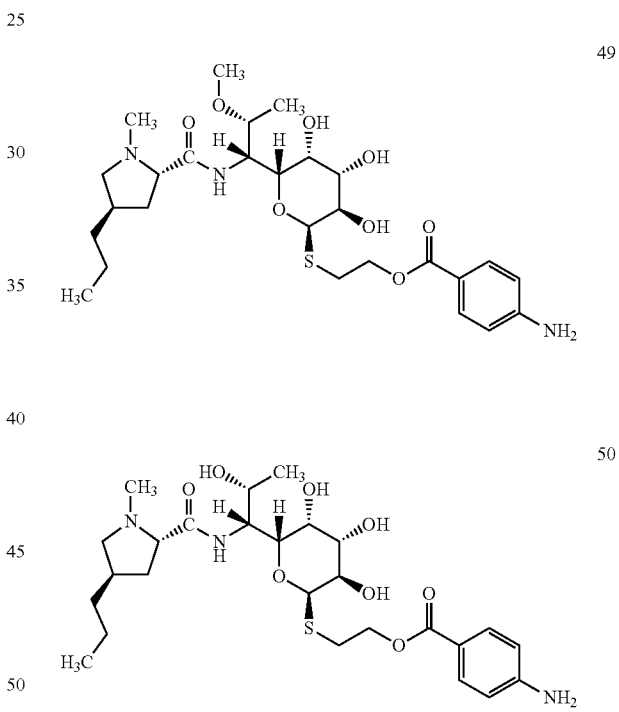

49

50

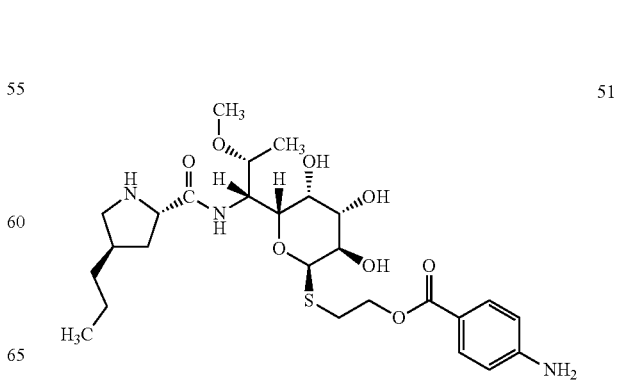

51

52

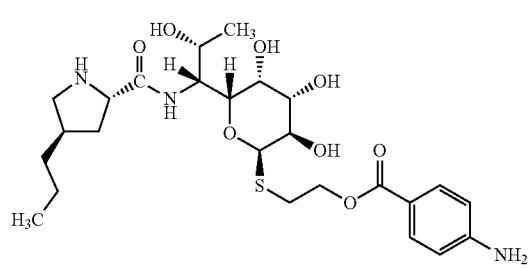

54

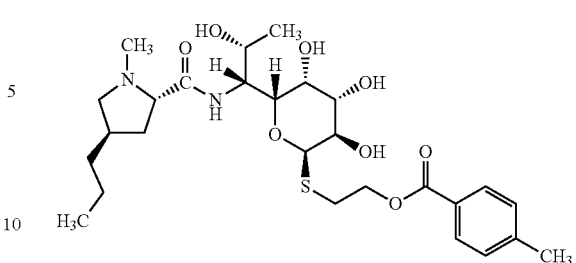

55

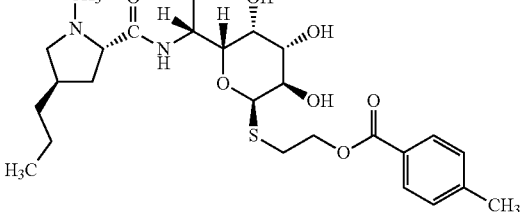

56

TABLE 15

Results of LC-MS analysis of the compounds 49-52

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 49 | 6.81 | 570.2850 | 570.2847 | 373.23; 126.13 |
| 50 | 5.50 | 556.2393 | 556.2692 | 359.22; 126.13 |
| 51 | 5.77 | 556.2393 | 556.2664 | 359.21; 112.11 |
| 52 | 3.72 | 542.2536 | 542.2545 | 345.20 |

LC-MS analyses were performed according to the procedure described in Example 3.

Example 16: In Vitro Enzymatic Preparation of Novel Lincosamide Compounds of Formula I Wherein R1=C3 Alkyl, R3=OH or OCH$_3$ (R Configuration), R4=H or CH$_3$, R21, R22, R24, R25 are H, R23 is CH$_3$ Reaction mixture 2 contained: 2 µM Ccb2, 2 µM Ccb1, 2 mM 4-methylbenzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 4-methylbenzoic acid was isolated from the reaction mixture according to the procedure of Example 3.

LC-MS Analysis

In total, four lincosamides were prepared: compounds 53-56 with the following structures and LC-MS parameters listed in Table 16.

53

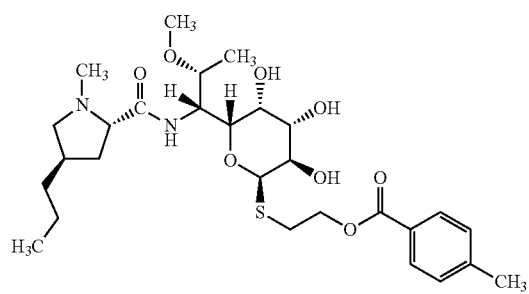

TABLE 16

Results of LC-MS analysis of the compounds 53-56

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 53 | 8.80 | 569.2897 | 569.2879 | 373.24; 126.13 |
| 54 | 8.08 | 555.2740 | 555.2748 | 359.22; 126.13 |
| 55 | 6.83 | 555.2740 | 555.2725 | 359.22 |
| 56 | 5.67 | 541.2583 | 541.2572 | 345.20 |

LC-MS analyses were performed according to the procedure described in Example 3.

Example 17: In Vitro Enzymatic Preparation of Novel Lincosamide Compounds of Formula I Wherein R1=C3 Alkyl, R3=OH or OCH$_3$ (R Configuration), R4=H or CH$_3$, R21, R22, R24, R25 are H, R23 is Cl Reaction mixture 2 contained: 2 µM Ccb2, 2 µM Ccb1, 2 mM 4-chlorobenzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 4-chlorobenzoic acid was isolated from the reaction mixture according to the procedure of Example 3.

LC-MS Analysis

In total, four lincosamides were prepared: compounds 57-60 with the following structures and LC-MS parameters listed in Table 17.

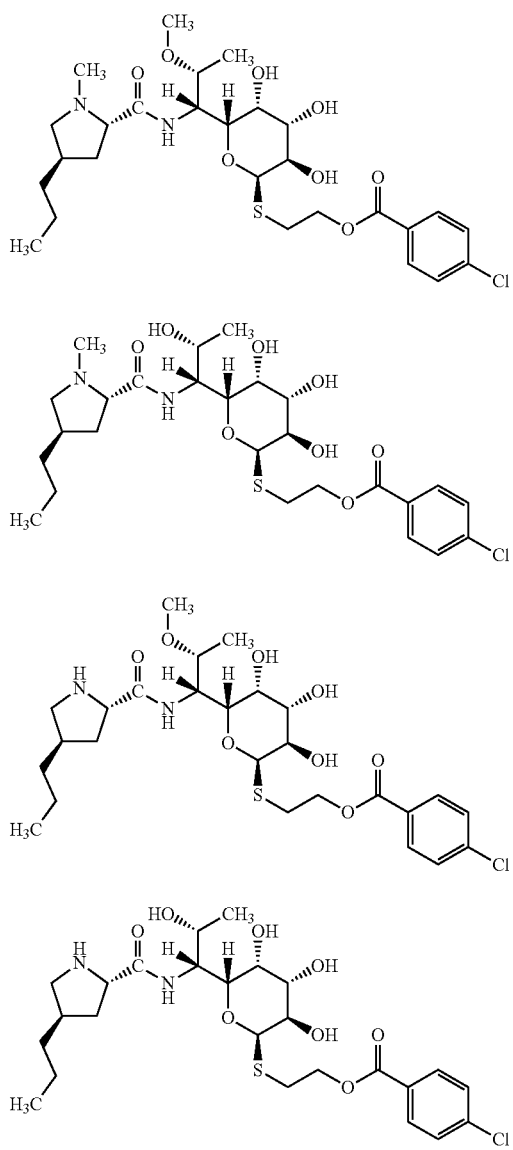

TABLE 17

Results of LC-MS analysis of the compounds 57-60

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 57 | 7.52 | 589.2351 | 589.2364 | 373.23; 126.13 |
| 58 | 7.60 | 575.2194 | 575.2183 | 359.22 |
| 59 | 7.54 | 575.2194 | 575.2197 | 359.22; 112.11 |
| 60 | 6.02 | 561.2037 | 561.2037 | 345.20 |

LC-MS analyses were performed according to the procedure described in Example 3.

Example 18: In Vitro Enzymatic Preparation of Novel Lincosamide Compounds of Formula I Wherein R1=C3 Alkyl, R3=OH or OCH$_3$ (R Configuration), R4=H or CH$_3$, R21, R25 are OH, R22-R24 are H Reaction mixture 2 contained: 2 μM Ccb2, 2 μM Ccb1, 2 mM 2,6-dihydroxybenzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 2,6-dihydroxybenzoic acid was isolated from the reaction mixture according to the procedure of Example 3.

LC-MS Analysis

In total, four lincosamides were prepared: compounds 61-64 with the following structures and LC-MS parameters listed in Table 18.

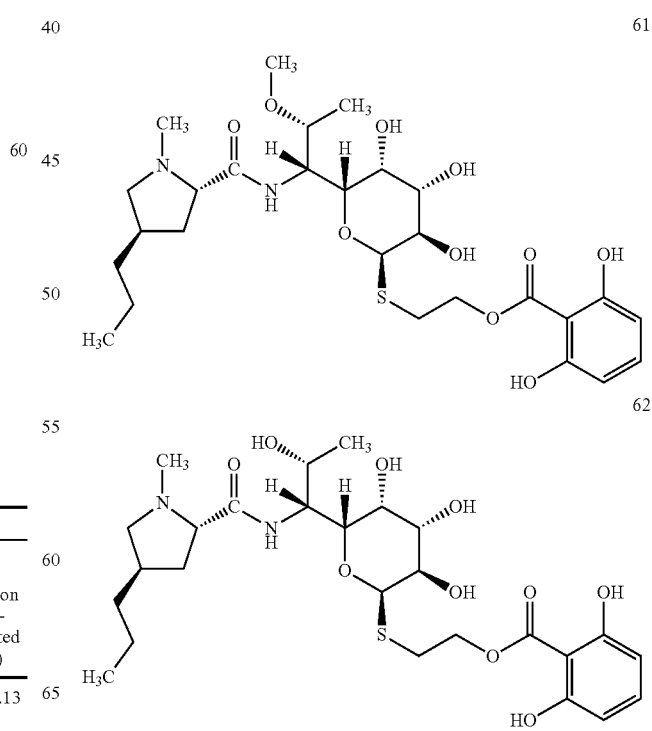

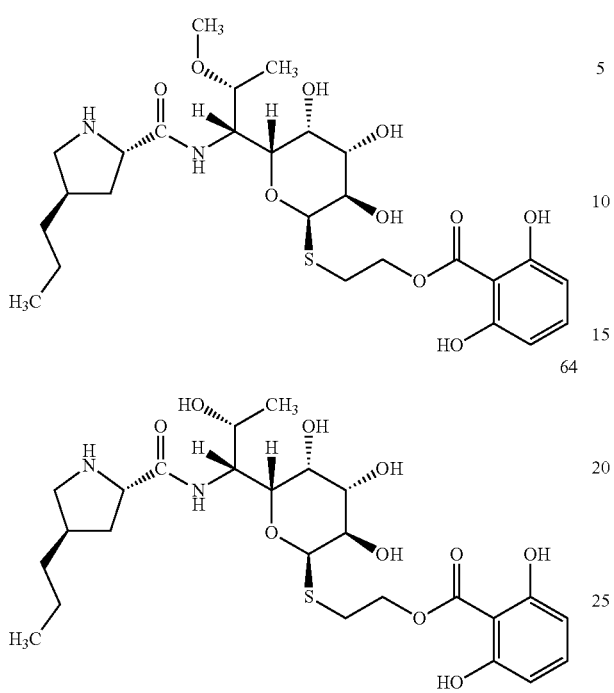

TABLE 18

Results of LC-MS analysis of the compounds 61-64

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 61 | 7.27 | 587.2639 | 587.2656 | 373.24; 126.13 |
| 62 | 5.90 | 573.2482 | 573.2484 | 359.22; 126.13 |
| 63 | 7.03 | 573.2482 | 573.2490 | 359.22 |
| 64 | 4.99 | 559.2325 | 559.2310 | 345.20 |

LC-MS analyses were performed according to the procedure described in Example 3.

Example 19: In Vitro Enzymatic Preparation of Novel Lincosamide Compounds of Formula I Wherein R1=C3 Alkyl, R3=OH or OCH$_3$ (R Configuration), R4=H or CH$_3$, R21, R22, R24 are H, R23, R25 are OH Reaction mixture 2 contained: 2 µM Ccb2, 2 µM Ccb1, 2 mM 2,4-dihydroxybenzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 2,4-dihydroxybenzoic acid was isolated from the reaction mixture according to the procedure of Example 3.

LC-MS Analysis

In total, four lincosamides were prepared: compounds 65-68 with the following structures and LC-MS parameters listed in Table 19.

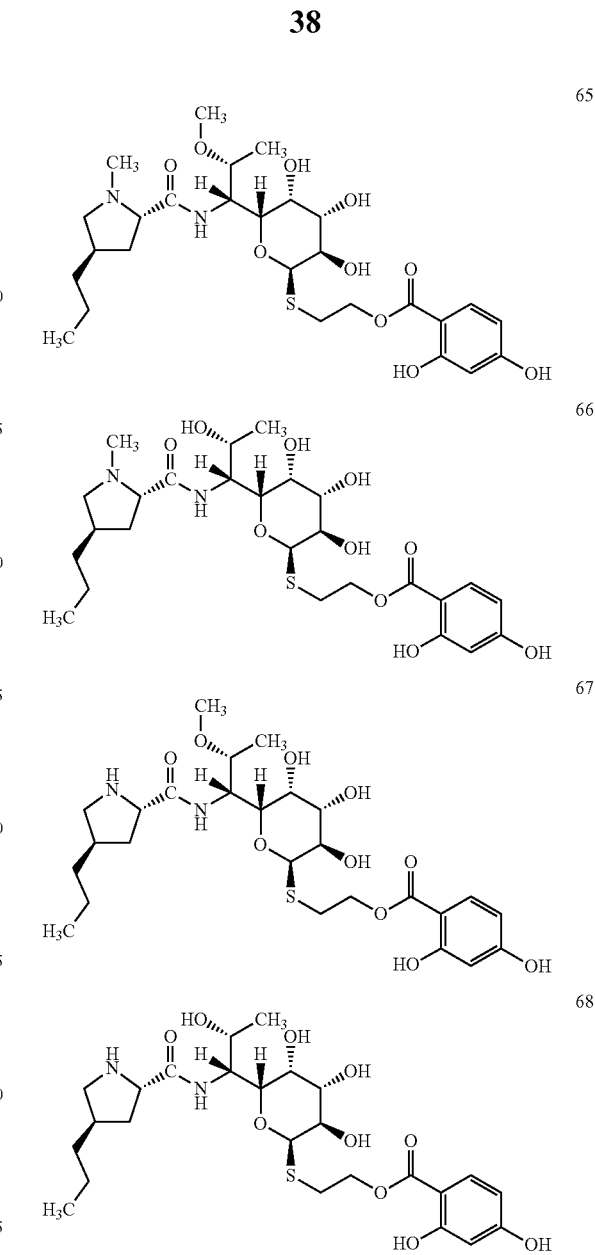

TABLE 19

Results of LC-MS analysis of the compounds 65-68

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 65 | 7.38 | 587.2639 | 587.2648 | 373.24; 126.13 |
| 66 | 6.05 | 573.2482 | 573.2483 | 359.22; 126.13 |
| 67 | 6.35 | 573.2482 | 573.2487 | 359.21 |
| 68 | 5.11 | 559.2325 | 559.2294 | 345.20 |

LC-MS analyses were performed according to the procedure described in Example 3.

Example 20: In Vitro Enzymatic Preparation of Novel Lincosamide Compounds of Formula I Wherein R1=C3 Alkyl, R3=OH or OCH₃ (R Configuration), R4=H or CH₃, R21, R22, R24 are H, R23 is NH₂, R25 is OH Reaction mixture 2 contained: 2 µM Ccb2, 2 µM Ccb1, 2 mM 4-amino-2-hydroxybenzoic acid, 4.5 mM adenosine triphosphate, 2 mM coenzyme A, 2 mM MgCl₂, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 4-amino-2-hydroxybenzoic acid was isolated from the reaction mixture according to the procedure of Example 3.

LC-MS Analysis

In total, four lincosamides were prepared: compounds 69-72 with the following structures and LC-MS parameters listed in Table 20.

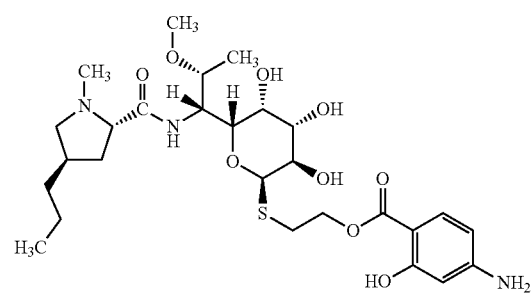

69

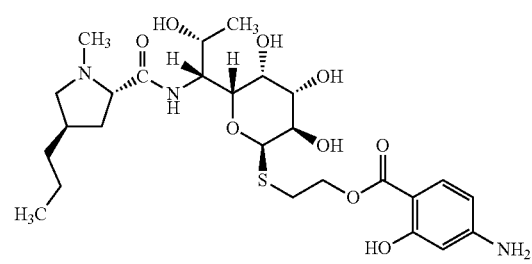

70

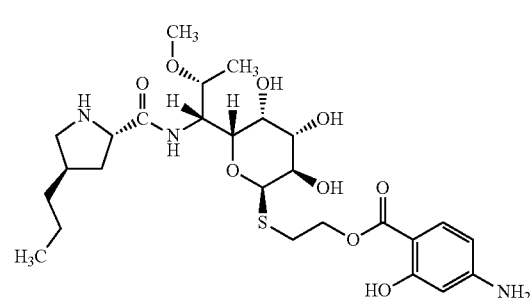

71

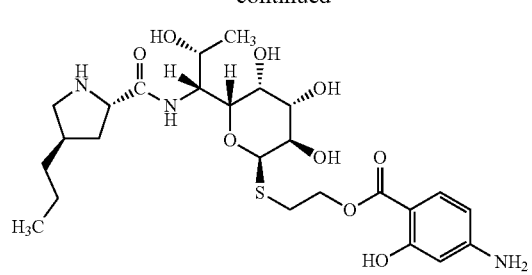

72

TABLE 20

Results of LC-MS analysis of the compounds 69-72

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 69 | 5.82 | 586.2799 | 586.2789 | 373.24; 126.13 |
| 70 | 4.97 | 572.2642 | 572.2646 | 359.22; 126.13 |
| 71 | 5.95 | 572.2642 | 572.2663 | 112.11 |
| 72 | 4.85 | 558.2485 | 558.2480 | 345.20 |

LC-MS analyses were performed according to the procedure described in Example 3.

Example 21: In Vitro Enzymatic Preparation of Novel Lincosamide Compounds of Formula I Wherein R1=C3 Alkyl, R3=OH or OCH₃ (R Configuration), R4=H or CH₃, R21, R22, R24 are H, R23 is NH₂, R25 is Cl Reaction mixture 2 contained: 2 µM Ccb2, 2 µM Ccb1, 2 mM 4-amino-2-chlorobenzoic acid, 4.5 mM adenosine triphosphate, 2 mM coenzyme A, 2 mM MgCl₂, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 4-amino-2-chlorobenzoic acid was isolated from the reaction mixture according to the procedure of Example 3.

LC-MS Analysis

In total, four lincosamides were prepared: compounds 73-76 with the following structures and LC-MS parameters listed in Table 21.

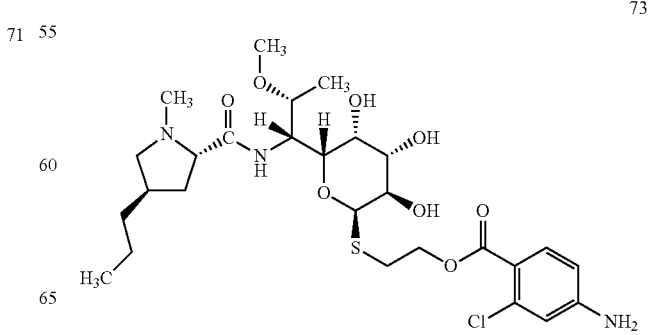

73

-continued

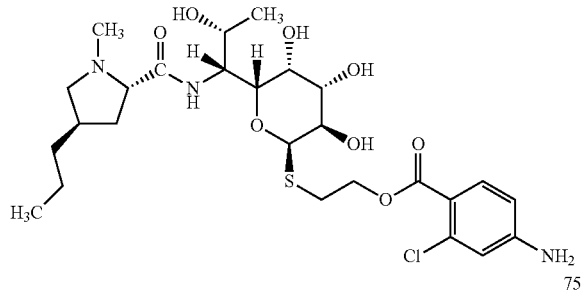

74

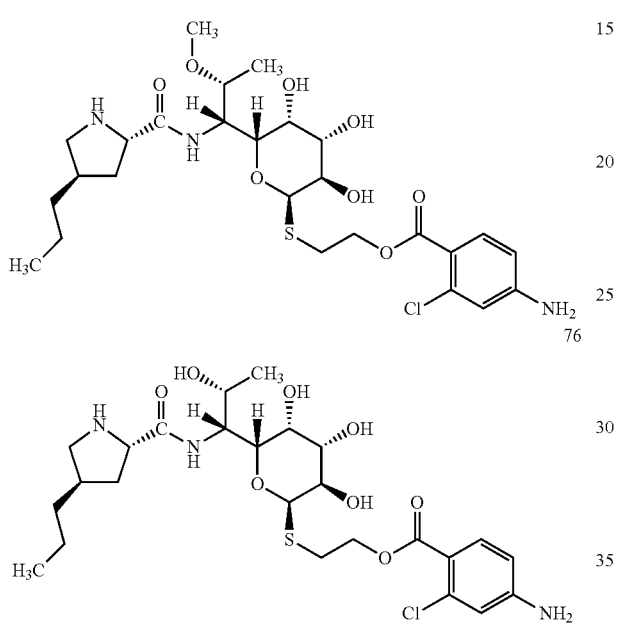

75

76 lincosamide precursor of formula II in a ratio of 1:1 and incubated at 30° C. for further 2 hours. The novel lincosamide with incorporated 2,4-dichlorobenzoic acid was isolated from the reaction mixture according to the procedure of Example 3.

LC-MS Analysis

In total, four lincosamides were prepared: compounds 77-80 with the following structures and LC-MS parameters listed in Table 22.

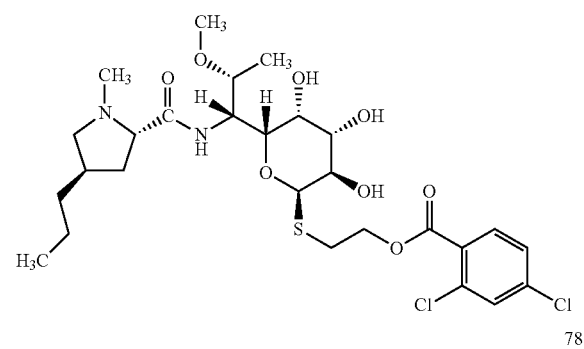

77

78

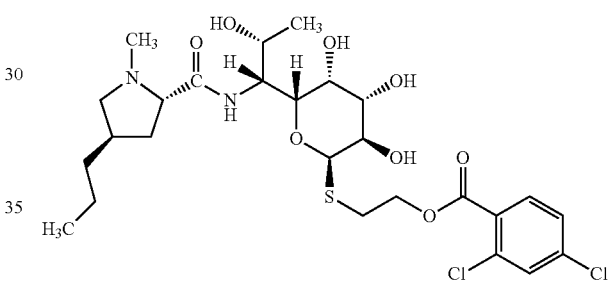

79

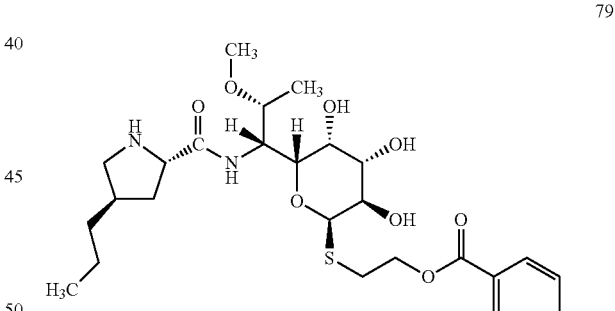

80

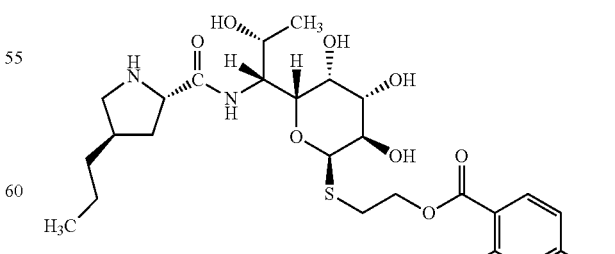

TABLE 21

Results of LC-MS analysis of the compounds 73-76

| Lincosamide | Retention time (min) | Pseudomolecular ion - theoretical value m/z for z = 1 | Major detected ion in MS spectrum (m/z) | Fragmentation in source - major detected ions (m/z) |
| --- | --- | --- | --- | --- |
| 73 | 7.05 | 604.2460 | 604.2453 | 373.24; 126.13 |
| 74 | 5.83 | 590.2303 | 590.2281 | 359.22; 126.13 |
| 75 | 5.38 | 590.2303 | 590.2286 | 359.22 |
| 76 | 4.38 | 576.2146 | 576.2155 | 345.20 |

LC-MS analyses were performed according to the procedure described in Example 3.

Example 22: In Vitro Enzymatic Preparation of Novel Lincosamide Compounds of Formula I Wherein R1=C3 Alkyl, R3=OH or OCH₃ (R Configuration), R4=H or CH₃, R21, R22, R24 are H, R23, R25 are Cl Reaction mixture 2 contained: 2 µM Ccb2, 2 µM Ccb1, 2 mM 2,4-dichlorobenzoic acid, 4.5 mM adenosine triphosphate, 2 mM coenzyme A, 2 mM MgCl₂, 100 mM Tris pH 7.5. Reaction mixture 2 was incubated at 30° C. for 30 min. Subsequently, reaction mixture 2 was mixed with reaction mixture 1 (prepared according to Example 2) containing the

TABLE 22

Results of LC-MS analysis of the compounds 77-80

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 77 | 9.78 | 623.1961 | 623.1944 | 373.24; 126.13 |
| 78 | 8.51 | 609.1804 | 609.1783 | 359.22; 126.13 |
| 79 | 8.37 | 609.1804 | 609.1724 | 359.22 |
| 80 | 6.48 | 595.1647 | 595.1632 | 345.20 |

LC-MS analyses were performed according to the procedure described in Example 3.

Example 23: In Vitro Enzymatic Preparation of Novel Lincosamide Compounds of Formula I Wherein R1=C3 Alkyl, R3=OH or OCH$_3$ (R Configuration), R4=H or CH$_3$, R21, R22, R25 are H, R23, R24 are OH Reaction mixture 2 contained: 2 µM Ccb2, 2 µM Ccb1, 2 mM 3,4-dihydroxybenzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 3,4-dihydroxybenzoic acid was isolated from the reaction mixture according to the procedure of Example 3.

LC-MS Analysis

In total, four lincosamides were prepared: compounds 81-84 with the following structures and LC-MS parameters listed in Table 23.

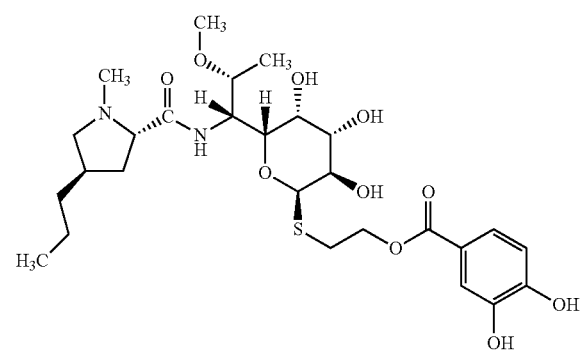

81

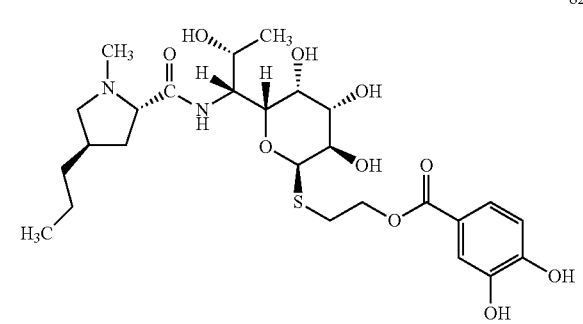

82

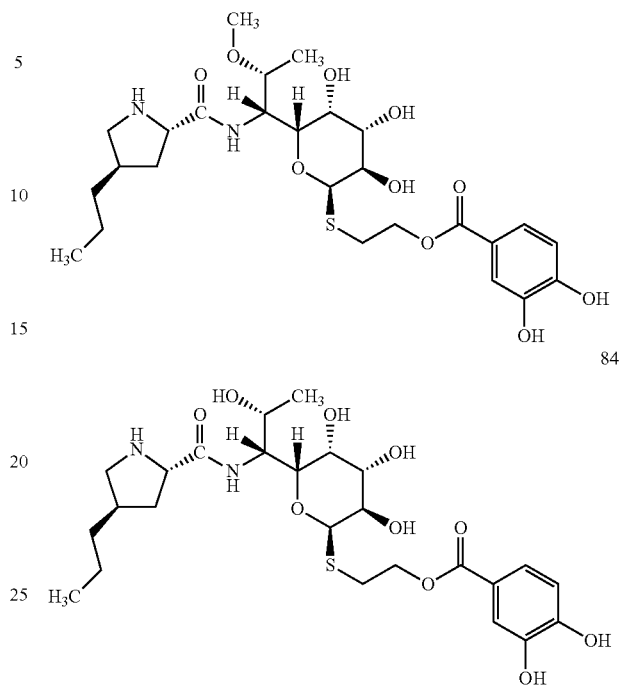

83

84

TABLE 23

Results of LC-MS analysis of the compounds 81-84

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 81 | 6.20 | 587.2639 | 587.2625 | 373.24; 126.13 |
| 82 | 5.00 | 573.2482 | 573.2493 | 359.22; 126.13 |
| 83 | 4.71 | 573.2482 | 573.2455 | 359.21 |
| 84 | 3.86 | 559.2325 | 559.2330 | 345.20 |

LC-MS analyses were performed according to the procedure described in Example 3.

Example 24: In Vitro Enzymatic Preparation of Novel Lincosamide Compounds of Formula I Wherein R1=C3 Alkyl, R3=OH or OCH$_3$ (R Configuration), R4=H or CH$_3$, R21, R22, R25 are H, R23, R24 are Cl Reaction mixture 2 contained: 2 µM Ccb2, 2 µM Ccb1, 2 mM 3,4-dichlorobenzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 3,4-dichlorobenzoic acid was isolated from the reaction mixture according to the procedure of Example 3.

LC-MS Analysis

In total, four lincosamides were prepared: compounds 85-88 with the following structures and LC-MS parameters listed in Table 24.

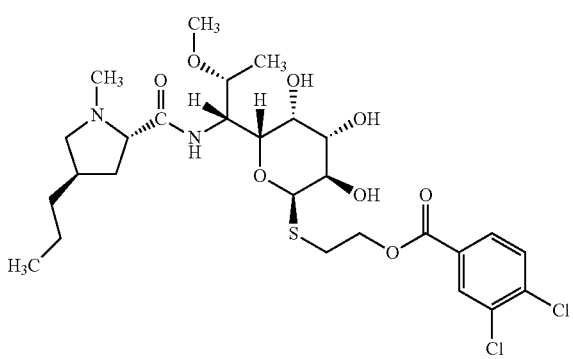

85

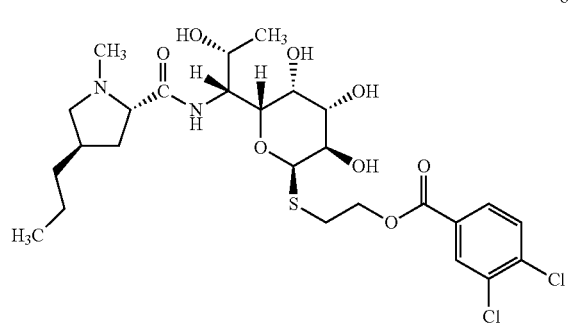

86

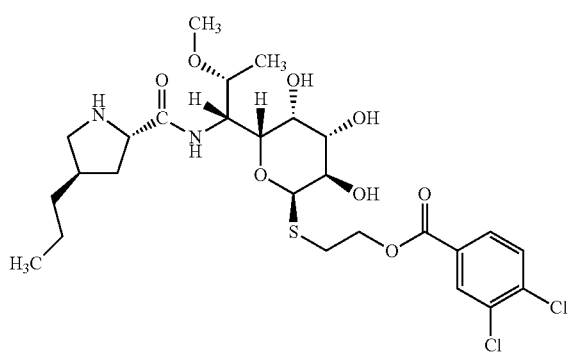

87

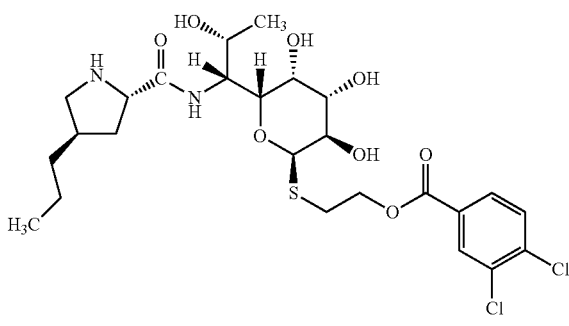

88

TABLE 24

Results of LC-MS analysis of the compounds 85-88

| Lincosamide | Retention time (min) | Pseudomolecular ion - theoretical value m/z for $z = 1$ | Major detected ion in MS spectrum (m/z) | Fragmentation in source - major detected ions (m/z) |
|---|---|---|---|---|
| 85 | 10.09 | 623.1961 | 623.1955 | 373.24; 126.13 |
| 86 | 8.77 | 609.1804 | 609.1821 | 359.22; 126.13 |
| 87 | 8.35 | 609.1804 | 609.1766 | 359.21 |
| 88 | 6.77 | 595.1647 | 595.1626 | 345.20 |

LC-MS analyses were performed according to the procedure described in Example 3.

Example 25: In Vitro Enzymatic Preparation of Novel Lincosamide Compounds of Formula I Wherein R1=C3 Alkyl, R3=OH or OCH₃ (R Configuration), R4=H or CH₃, R21, R23, R25 are H, R22, R24 are OH Reaction mixture 2 contained: 2 µM Ccb2, 2 µM Ccb1, 2 mM 3,5-dihydroxybenzoic acid, 4.5 mM adenosine triphosphate, 2 mM coenzyme A, 2 mM MgCl₂, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 3,5-dihydroxybenzoic acid was isolated from the reaction mixture according to the procedure of Example 3.

LC-MS Analysis

In total, four lincosamides were prepared: compounds 89-92 with the following structures and LC-MS parameters listed in Table 25.

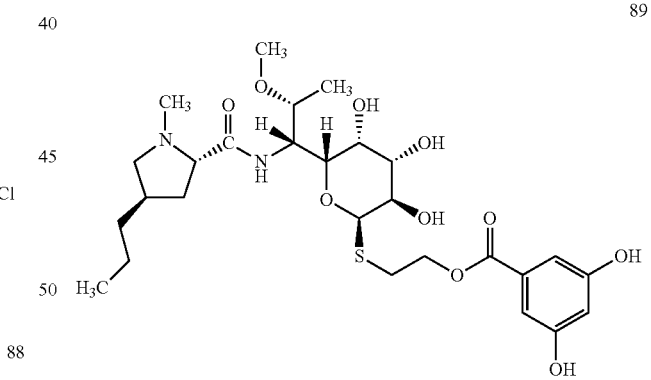

89

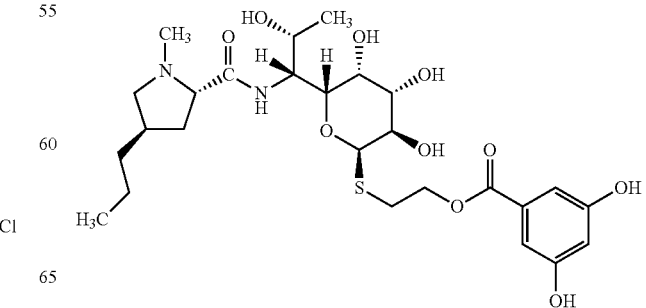

90

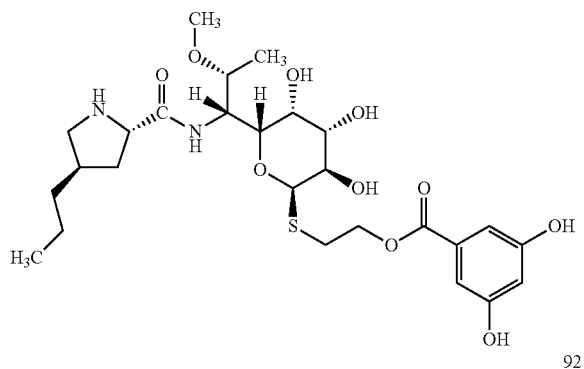

91

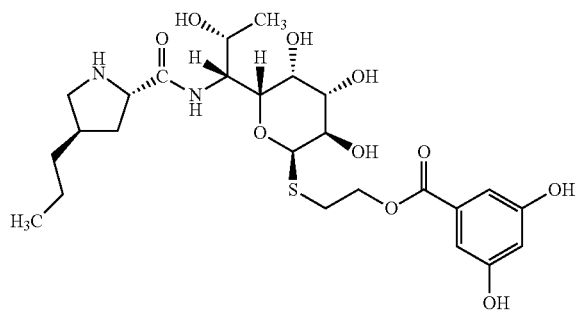

92

TABLE 25

Results of LC-MS analysis of the compounds 89-92

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 89 | 5.95 | 587.2639 | 587.2632 | 373.24; 126.13 |
| 90 | 4.94 | 573.2482 | 573.2468 | 359.22; 126.13 |
| 91 | 4.40 | 573.2482 | 573.2460 | 359.21 |
| 92 | 3.48 | 559.2325 | 559.2320 | 345.20 |

Example 26: In Vitro Enzymatic Preparation of Novel Lincosamide Compounds of Formula I Wherein R1=C3 Alkyl, R3=OH or OCH$_3$ (R Configuration), R4=H or CH$_3$; R21, R23, R25 are H; R22, R24 are Cl Reaction mixture 2 contained: 2 μM Ccb2, 2 μM Ccb1, 2 mM 3,5-dichlorobenzoic acid, 4.5 mM adenosine triphosphate, 2 mM coenzyme A, 2 mM MgCl$_2$, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 3,5-dichlorobenzoic acid was isolated from the reaction mixture according to the procedure of Example 3.

LC-MS Analysis

In total, four lincosamides were prepared: compounds 93-96 with the following structures and LC-MS parameters listed in Table 26.

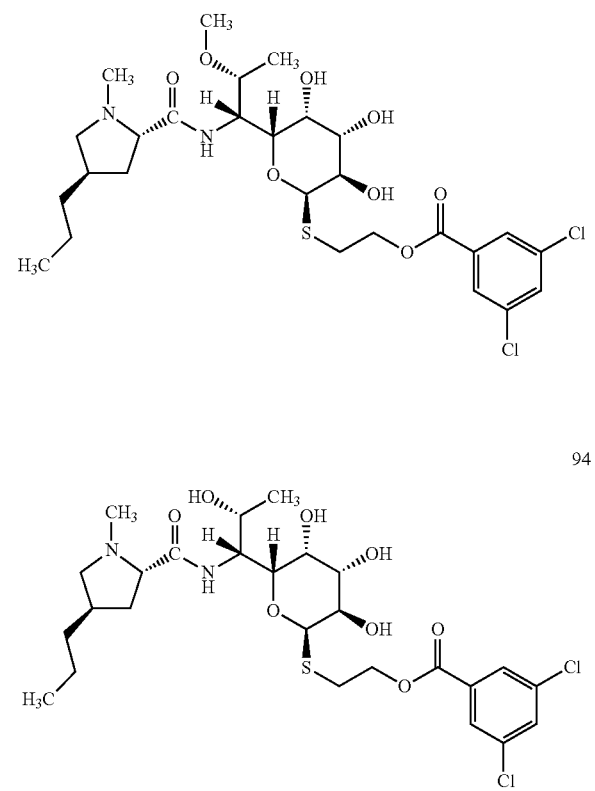

TABLE 26

Results of LC-MS analysis of the compounds 93-96

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 93 | 10.37 | 623.1961 | 623.1967 | 373.24; 126.13 |
| 94 | 8.87 | 609.1804 | 609.1788 | 359.22; 126.13 |
| 95 | 8.10 | 609.1804 | 609.1755 | 359.22 |
| 96 | 6.80 | 595.1647 | 595.1620 | 345.20 |

LC-MS analyses were performed according to the procedure described in Example 3.

Example 27: In Vitro Enzymatic Preparation of Novel Lincosamide Compounds of Formula I Wherein R1=C3 Alkyl, R3=OH or OCH₃ (R Configuration), R4=H or CH₃; R22, R23, R25 are H; R21, R24 are OH Reaction mixture 2 contained: 2 µM Ccb2, 2 µM Ccb1, 2 mM 2,5-dihydroxybenzoic acid, 4.5 mM adenosine triphosphate, 2 mM coenzyme A, 2 mM MgCl₂, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 2,5-dihydroxybenzoic acid was isolated from the reaction mixture according to the procedure of Example 3.

LC-MS Analysis

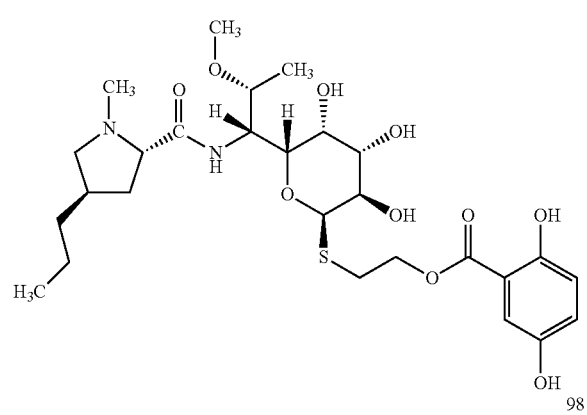

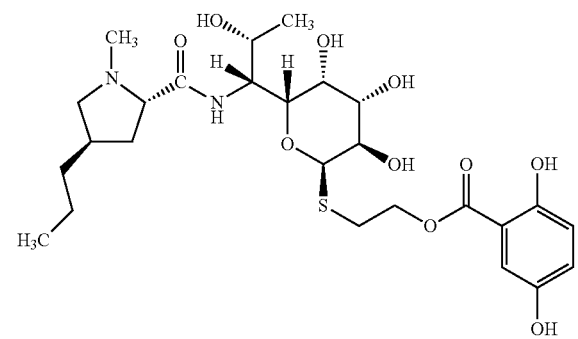

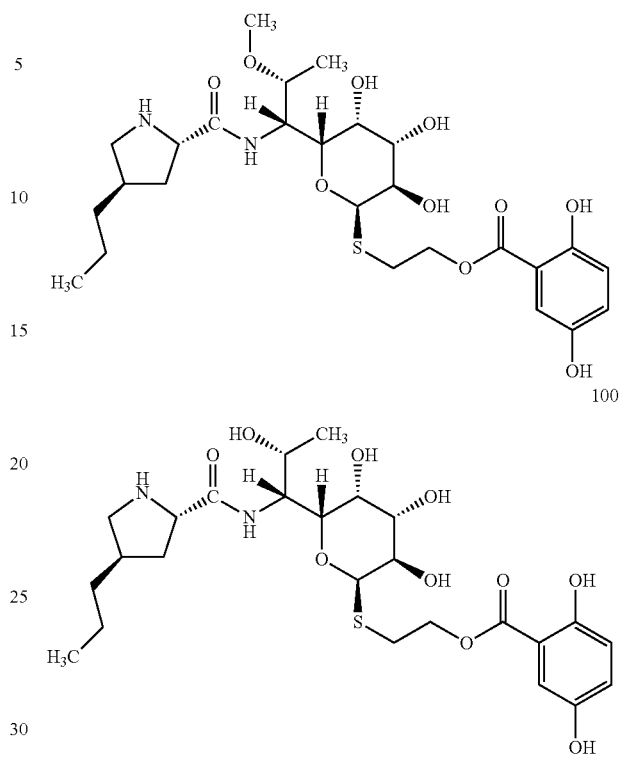

TABLE 27

Results of LC-MS analysis of the compounds 97-100

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 97 | 7.46 | 587.2639 | 587.2649 | 373.24; 126.13 |
| 98 | 6.09 | 573.2482 | 573.2463 | 359.22; 126.13 |
| 99 | 6.18 | 573.2482 | 573.2466 | 359.22 |
| 100 | 4.32 | 559.2325 | 559.2320 | 345.20 |

LC-MS analyses were performed according to the procedure described in Example 3.

Example 28: In Vitro Enzymatic Preparation of Novel Lincosamide Compounds of Formula I Wherein R1=C3 Alkyl, R3=OH or OCH₃ (R Configuration), R4=H or CH₃; R21, R25 are H; R22-R24 are OH Reaction mixture 2 contained: 2 µM Ccb2, 2 µM Ccb1, 2 mM 3,4,5-trihydroxybenzoic acid, 4.5 mM adenosine triphosphate, 2 mM coenzyme A, 2 mM MgCl₂, 100 mM Tris pH 7.5. Reaction mixture 2 was incubated at 30° C. for 30 min. Subsequently, reaction mixture 2 was mixed with reaction mixture 1 (prepared according to Example 2) containing the lincosamide precursor of formula II in a ratio of 1:1 and incubated at 30° C. for further 2 hours. The novel lincosamide with incorporated 3,4,5-trihydroxybenzoic acid was isolated from the reaction mixture according to the procedure of Example 3.

LC-MS Analysis

In total, four lincosamides were prepared: compounds 101-104 with the following structures and LC-MS parameters listed in Table 28.

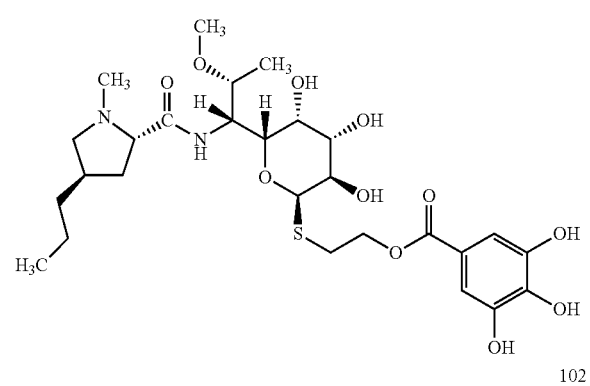

101

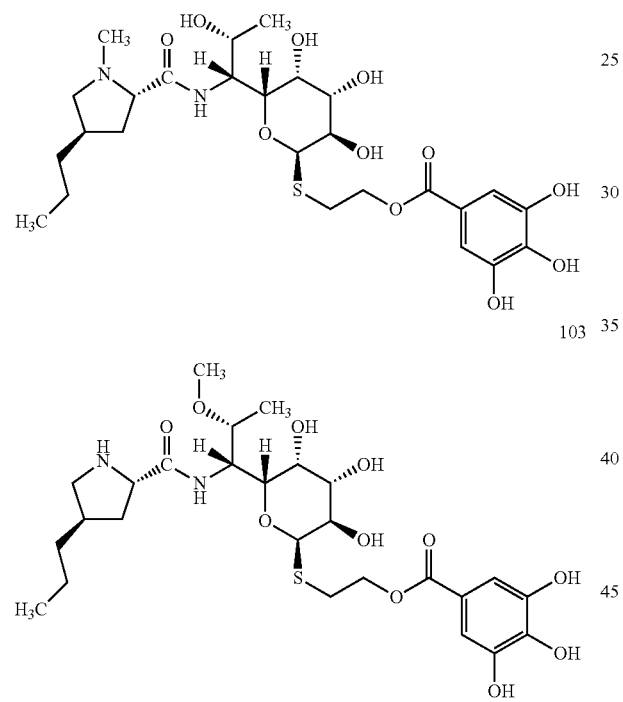

102

103

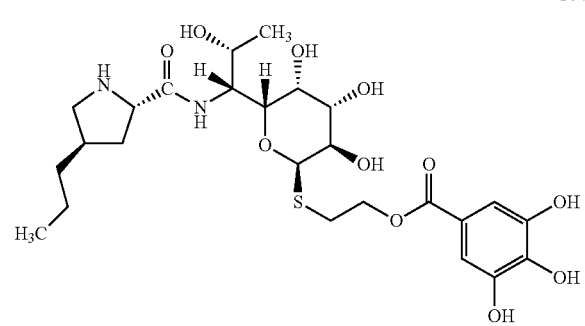

104

TABLE 28

Results of LC-MS analysis of the compounds 101-104

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 101 | 4.65 | 603.2588 | 603.2582 | 373.24; 126.13 |
| 102 | 3.77 | 589.2431 | 589.2422 | 359.22; 126.13 |
| 103 | 4.76 | 589.2431 | 589.2427 | 359.21 |
| 104 | 3.08 | 575.2274 | 575.2269 | 345.20 |

LC-MS analyses were performed according to the procedure described in Example 3.

Example 29: Preparation of Novel Lincosamide Compounds of Formula I Wherein R1=C3 Alkyl, R3=Cl (S Configuration), R4=H or CH$_3$; R21-R24 are H; R25 is OH

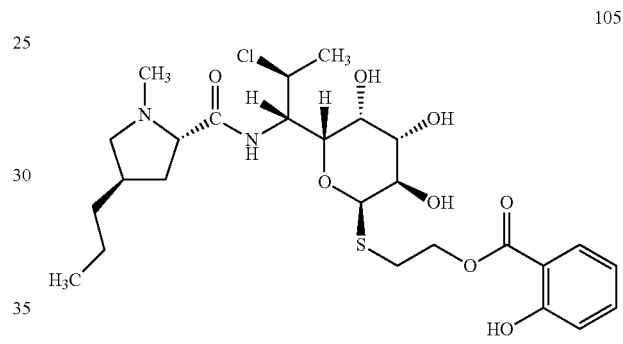

105

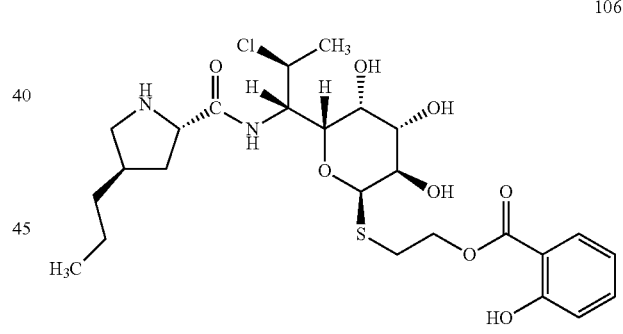

106

Preparation of novel lincosamides wherein R3=Cl starts from the lincosamides prepared in Example 3, wherein R3=OH (R configuration). These are synthetically chlorinated by the following procedure. To a suspension of N-(chloromethylene)-N-methylmethaniminium chloride (11 mmol) in dichloromethane (3.5 mL) vigorously stirred under an inert atmosphere (Ar) with cooling with an external bath containing water and ice was added portionwise over 15 min lincosamide (2 mmol) and 3-tert-butyl-4-hydroxy-5-methylphenyl sulfide (9 mg) to give the addition product. The cooling was stopped, the reaction mixture was stirred for 2 h at room temperature and then heated at 60° C. for 6 h, then for a further 4 h at 68° C. Subsequently, the reaction mixture was cooled to 0° C. and slowly added dropwise to a solution of NaOH (0.66 g) in a mixture of water and ice (6 g) cooled with an external acetone/dry ice (−78° C.) external bath so that the reaction mixture temperature did not exceed 21° C.

During the addition of the reaction mixture, the pH was maintained at about 6 by the addition of a further portion of aqueous NaOH. The pH of the mixture was then raised to 10.5 and stirred for 2 h, then adjusted to pH=7 and stirred overnight. The mixture was then cooled to 0° C. with ice and water, the pH was reduced to 1.5 with HCl and extracted with $CH_2Cl_2$ (5×5 mL). Each of the organic phases was washed with 7.5 ml of a dilute HCl solution (pH 1.5). The aqueous phases were combined, alkalized with dilute NaOH to pH=10.5 and extracted with $CH_2Cl_2$ (5×5 mL). Each organic phase was washed with 2×7.5 ml phosphate buffer (0.5 M, pH=6.2). The organic phases were combined, dried with anhydrous $Na_2SO_4$, filtered and concentrated. The resulting oil was dissolved in ethyl acetate (20 mL), evaporated on a vacuum evaporator and this operation was repeated once more. The oil was dissolved in ethyl acetate and subjected to decolorization with charcoal (50 mg) for 30 min. Subsequently, it was filtered through Celite and concentrated to an oil. Subsequently dissolved in ethyl acetate (8 mL) and absolute ethanol (2 mL) and at vigorous stirring, concentrated HCl was added to a final pH of 0.5. The resulting slurry was stirred for 1 hour at room temperature, then for 30 min at 0° C. The crystals were filtered off, washed with ethyl acetate (1 mL) and dried overnight at 80° C. under vacuum. Thus ethanol solvate of lincosamide hydrochloride of formula I was obtained wherein R3=Cl (S configuration) in a total yield of about 80%.

Preparation of hydrochloride hydrate: The ethanol solvate prepared by the above process is dissolved in water, evaporated to syrup, dissolved in hot acetone, then slowly cooled to room temperature for 4 hours. Subsequent cooling of the acetone solution to 0° C. causes precipitation of the lincosamide hydrochloride hydrate crystals. These are filtered off after 30 min at 0° C. and air-dried. The yield is about 90%.

Example 30: Preparation of a Precursor of Formula III Wherein R1 is C4-C6 Alkyl, R3 is OH (R Configuration), R4 is H or $CH_3$ The preparation is analogous to the procedure for the preparation of the precursors of formula III wherein R1=C3 alkyl as described in Example 1 except that the bacterial culture incubated in YEME medium is supplemented with 50 μl 200 mM 4-butyl-L-proline (for R1=C4 alkyl) or 4-pentyl-L-proline (for R1=C5 alkyl) or 4-hexyl-L-proline (for R1=C6 alkyl). Isolation of the precursor of formula III is then carried out analogously to the procedure described in Example 1.

LC-MS Analysis

Two precursors, 107, 108 having the following structures and the LC-MS parameters listed in Table 29, were prepared.

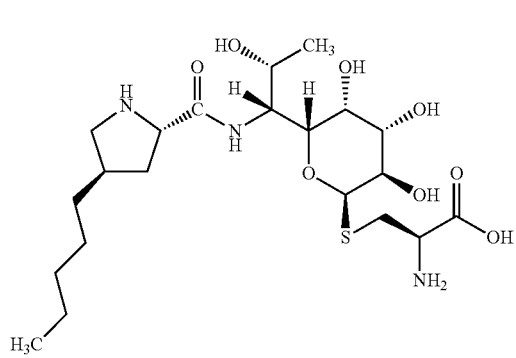

107

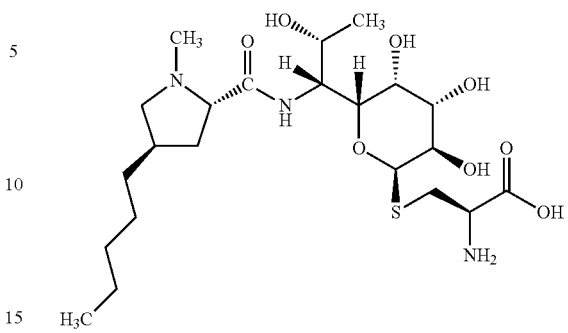

108

TABLE 29

Results of LC-MS analysis of the compounds 107, 108

| Lincosamide | Retention time (min) | Pseudomolecular ion - theoretical value m/z for z = 1 | Major detected ion in MS spectrum (m/z) | Fragmentation in source - major detected ions (m/z) |
|---|---|---|---|---|
| 107 | 4.21 | 494.2536 | 494.2499 | 373.23, 140.14 |
| 108 | 5.11 | 508.2693 | 508.2666 | 387.25; 154.16 |

LC-MS analyses were performed according to the procedure described in Example 3.

Example 31: Preparation of the Precursor of Formula II, Wherein R1 is C4-C6 Alkyl, R3 is OH or $OCH_3$ (R Configuration), R4 is H or $CH_3$ Reaction mixture 1 contained: 20 μM CcbF, 20 μM Ccb5, 200 μM lincosamide precursor of formula III wherein R1 is C4-C6 alkyl, R3 is OH, R4 is H or $CH_3$ and R5 is H—its preparation is described in Example 30, 200 μM pyridoxal-5-phosphate, 100 mM Tris pH 7.5. In the case of preparing new lincosamide compounds according to formula II, wherein R3=$OCH_3$, the reaction mixture additionally contained 20 μM Ccb4 and 4 mM S-adenosylmethionine. Reaction mixture 1 was incubated at 30° C. for 2 h. Preparation of heterologous proteins is described in Example 2.

Example 32: In Vitro Enzymatic Preparation of Novel Lincosamide Compounds of Formula I Wherein R1=C4-C6 Alkyl, R3=$OCH_3$ or OH (R Configuration), R4=H or $CH_3$, R21-R24 are H and R25 is OH Reaction mixture 2 contained: 2 μM Ccb2, 2 μM Ccb1, 2 mM salicylic acid, 4.5 mM adenosine triphosphate, 2 mM coenzyme A, 2 mM $MgCl_2$, 100 mM Tris pH 7.5. Reaction mixture 2 was incubated at 30° C. for 30 min. Subsequently, reaction mixture 2 was mixed in the ratio 1:1 with reaction mixture 1 (preparation according to example 32) containing the lincosamide precursor of formula II and incubated at 30° C. for further 2 h. Lincosamide isolation was performed as described in Example 3.

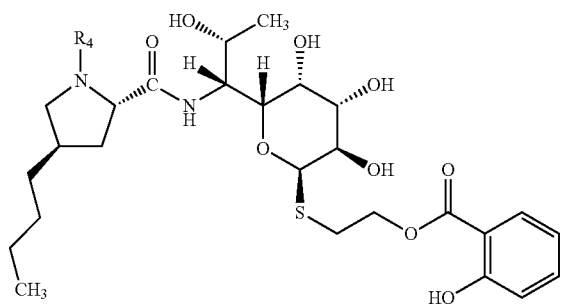

109a: R4 = H
109b: R4 = CH3

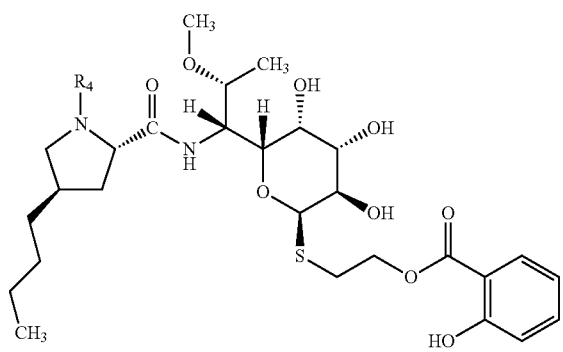

110a: R4 = H
110b: R4 = CH3

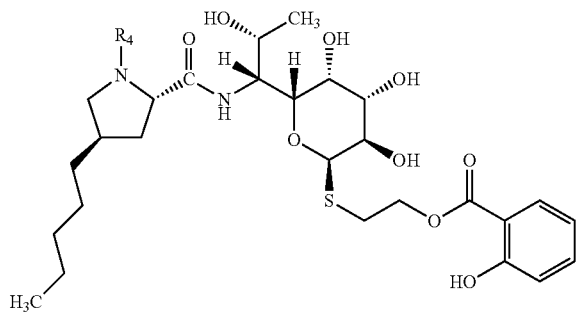

111a: R4 = H
111b: R4 = CH3

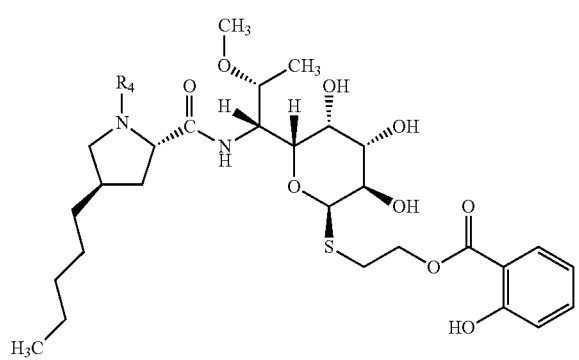

112a: R4 = H
112b: R4 = CH3

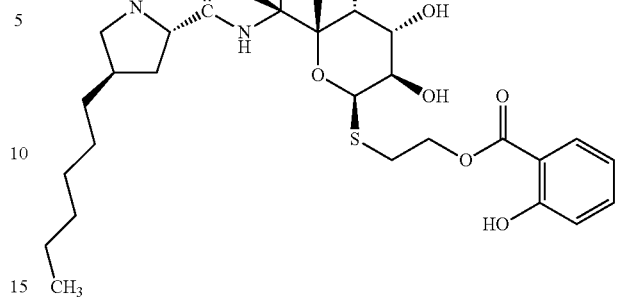

113a: R4 = H
113b: R4 = CH3

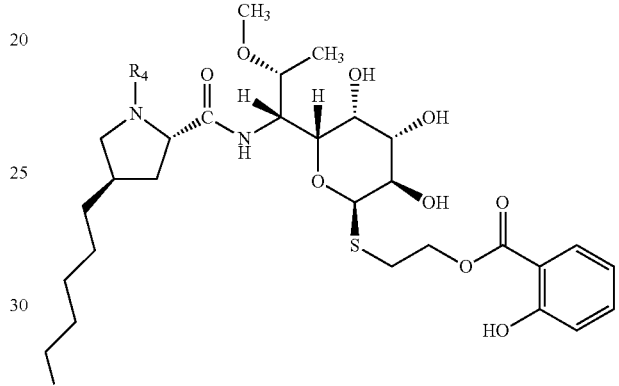

114a: R4 = H
114b: R4 = CH3

Example 33: Preparation of Novel Lincosamide Compounds of Formula I Wherein R1=C4-C6 Alkyl, R3=Cl (S Configuration), R4=H or CH3, R21-R24 are H and R25 is OH Preparation of novel lincosamides wherein R1=C4-C6 alkyl and R3=Cl starts from the lincosamides prepared in Example 32, wherein R3=OH (R configuration). They are synthetically chlorinated by the same chlorination procedure as described in Example 29.

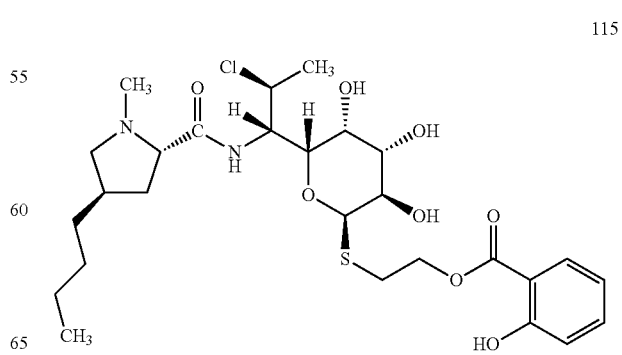

115

116
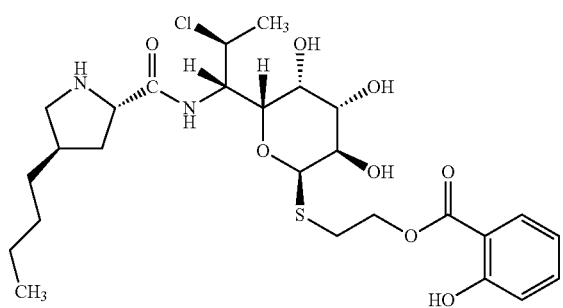
117
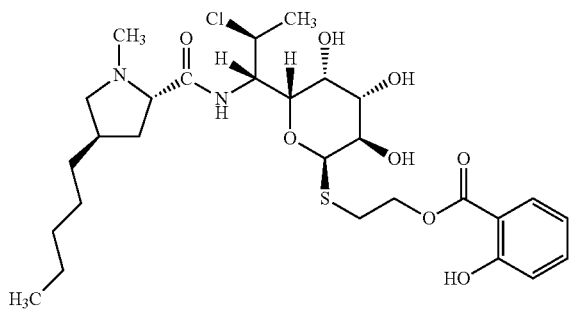
118
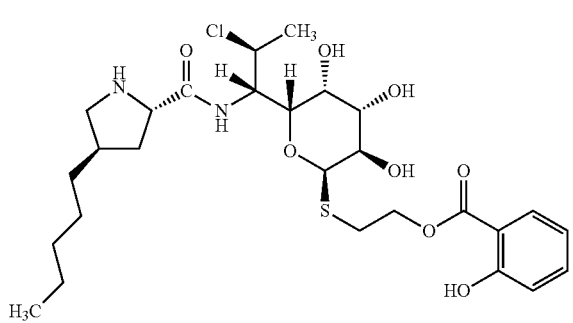
119
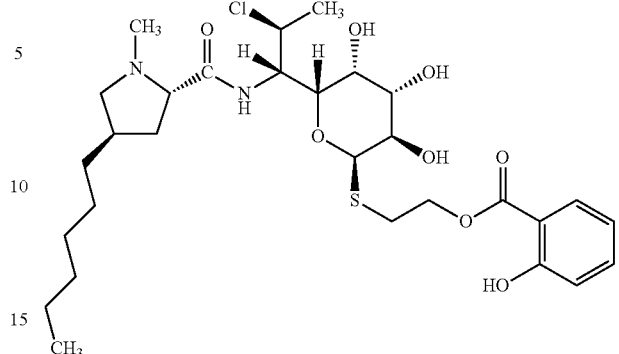
119
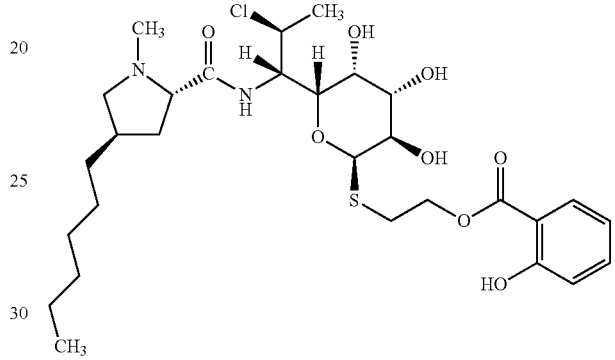
120
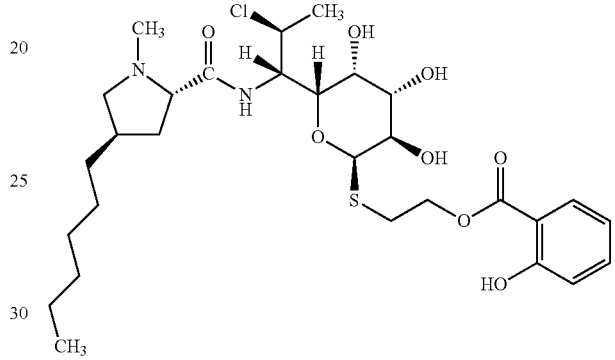

The invention claimed is:

1. Lincosamides of general formula I

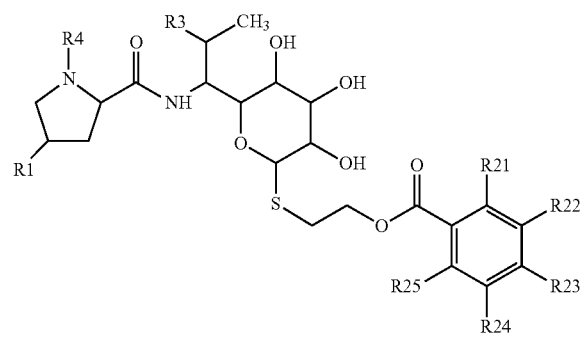

(I)

wherein
R1 is selected from C2-C8 alkyl or C2-C8 alkenyl;
R3 is selected from OH, O(C1-C4 alkyl), SH, S(C1-C4 alkyl) or halogen;
R4 is H or C1-C3 alkyl;
each of R21, R22, R23, R24, R25 is independently selected from the group consisting of H, OH, C1-C4 alkyl, C1-C4 alkenyl, C1-C4 alkynyl, halogen, O(C1-C4 alkyl), O(C1-C4 alkenyl), O(C1-C4 alkynyl), $NH_2$, $N(C1-C4\ alkyl)_2$, $N(C1-C4\ alkenyl)_2$, $N(C1-C4\ alkynyl)_2$;
and pharmaceutically acceptable salts thereof.

2. Lincosamides according to claim 1, wherein R1 is C3-C6 alkyl.

3. Lincosamides according to claim 1, wherein R3 is OH, $OCH_3$, $OCH_2CH_3$ or Cl.

4. Lincosamides according to claim 1, wherein R4 is H or $CH_3$.

5. Lincosamides according to claim 1, wherein each of R21, R22, R23, R24, R25 is independently selected from the group consisting of H, OH, $CH_3$, $CH_2CH_3$, Cl, Br, I, $OCH_3$, $OCH_2CH_3$, $NH_2$.

6. Lincosamides according to claim 1, wherein the general formula I has a configuration on chiral centers shown below:

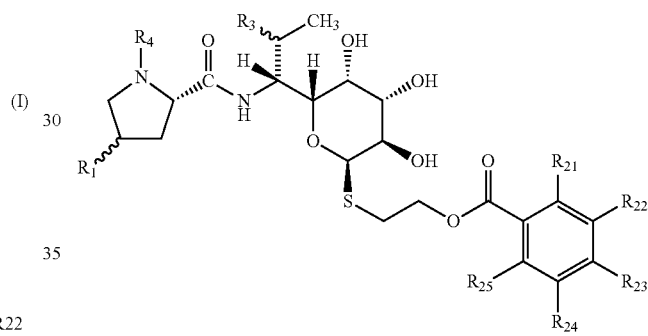

(I)

wherein R1 and R3 have configurations R or S.

7. A method of preparation of compounds of general formula I according to claim 1, characterized in that it comprises a step of enzymatically catalyzed activation of R21-, R22-, R23-, R24- and R25-substituted benzoic acid derivative by coenzyme A attachment, and a step of enzymatically catalyzed esterification of a precursor of formula II

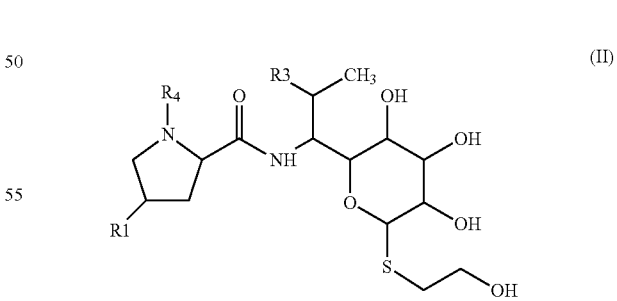

(II)

with the conjugate of coenzyme A and R21-, R22-, R23-, R24- and, R25-substituted benzoic acid derivative, wherein the substituents R1, R3, R4 in formula II are as defined for formula I.

8. The method according to claim 7, characterized in that for the enzymatically catalyzed activation of R21-, R22-, R23-, R24- and R25-substituted benzoic acid derivative by coenzyme A attachment, an enzymatically active protein containing a celesticetin biosynthetic protein Ccb2, or containing a Ccb2-like protein having at least 95% identity with the amino acid sequence of Ccb2 is used, and/or for the esterification of the precursor of formula II, an enzymatically active protein containing a celesticetin biosynthetic protein Ccb1, or containing a Ccb1-like protein having at least 95% identity with the amino acid sequence of Ccb1 is used.

9. The method according to claim 7, wherein the precursor of general formula II is obtained by enzymatic transformation of a precursor of general formula III

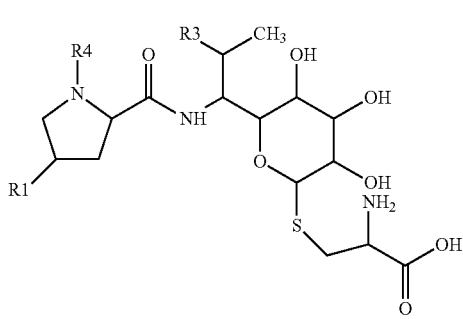

(III)

by action of an enzymatically active protein containing celesticetin biosynthetic protein CcbF, and/or an enzymatically active protein containing celesticetin biosynthetic protein Ccb5, and/or optionally an enzymatically active protein containing celesticetin biosynthetic protein Ccb4, or of an enzymatically active protein containing celesticetin biosynthetic protein having at least 95% identity with CcbF, and/or an enzymatically active protein containing celesticetin biosynthetic protein having at least 95% identity with Ccb5, and/or an enzymatically active protein containing celesticetin biosynthetic protein having at least 95% identity with optionally Ccb4, wherein in formula III the substituents R1, R3, R4 are as defined for formula I.

10. The method according to claim 7, wherein the enzymatically catalyzed activation of R21-, R22-, R23-, R24- and R25-substituted benzoic acid derivative by coenzyme A attachment and/or the enzymatically catalyzed esterification of a precursor of formula II with the conjugate of the R21-, R22-, R23-, R24- and R25-substituted benzoic acid derivative with coenzyme A are carried out biosynthetically using a microorganism carrying the coding sequences of celesticetin biosynthetic proteins Ccb1 and/or Ccb2, or biosynthetic proteins having at least 95% identity of the amino acid sequence with Ccb1 and/or Ccb2.

11. The method according to claim 10, wherein the microorganism further carries coding sequences of celesticetin biosynthetic proteins Ccb5, CcbF, and optionally Ccb4, or biosynthetic proteins having at least 95% identity with Ccb5, CcbF, and optionally Ccb4, and the method starts from the precursor of formula III.

12. The method according to claim 11, wherein the microorganism further carries also coding sequences of the lincomycin and/or celesticetin biosynthetic proteins, needed in combination for biosynthesis of the precursor of formula III in a cell.

13. The method according to claim 10, wherein the biosynthetically obtained compound of general formula I is further synthetically modified, by chlorination in position 7 of the sugar residue to form a compound of formula I with R3=Cl.

14. A method of inhibiting or killing microbes, comprising the step of administering a therapeutically effective amount of a lincosamide of general formula I according to claim 1 to a subject in need of such treatment.

15. A method of inhibiting or killing of bacterial or unicellular eukaryotic parasitic microorganisms, comprising the step of administering a therapeutically effective amount of a lincosamide of general formula I according to claim 1 to a subject in need of such treatment.

16. The method according to claim 15, wherein the bacterial and unicellular eukaryotic parasitic microorganisms are selected from Gram-positive bacteria, parasites of the phylum Apicomplexa comprising target organelles apicoplasts, and organisms of genus *Plasmodium, Toxoplasma, Babesia, Theileria* and *Coccidia*.

17. Lincosamides according to claim 2, wherein R1 is selected from propyl, butyl, pentyl, hexyl.

18. Lincosamides according to claim 6, wherein the chiral center bearing the group R1 has the configuration R.

19. Lincosamides according to claim 6, wherein the chiral center bering the group R3 has the configuration R, when R3=OH, OCH3, OCH2CH3, and configuration S, when R3=halogen.

20. The method according to claim 10, wherein the microorganism is a microorganism of the class Actinobacteria.

21. The method according to claim 10, wherein the microorganism is a microorganism of the genus *Streptomyces*.

* * * * *